United States Patent
Hubbell

(10) Patent No.: US 8,934,689 B2
(45) Date of Patent: Jan. 13, 2015

(54) FEATURE INTENSITY RECONSTRUCTION OF BIOLOGICAL PROBE ARRAY

(71) Applicant: Affymetrix, Inc., Santa Clara, CA (US)

(72) Inventor: Earl A. Hubbell, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 13/663,673

(22) Filed: Oct. 30, 2012

(65) Prior Publication Data
US 2013/0142408 A1  Jun. 6, 2013

Related U.S. Application Data

(63) Continuation of application No. 13/186,167, filed on Jul. 19, 2011, now Pat. No. 8,369,596, which is a continuation of application No. 11/769,600, filed on Jun. 27, 2007, now Pat. No. 8,009,889.

(60) Provisional application No. 60/817,126, filed on Jun. 27, 2006.

(51) Int. Cl.
*G06K 9/00* (2006.01)
*G06F 19/20* (2011.01)

(52) U.S. Cl.
CPC .............. *G06K 9/00* (2013.01); *G06K 2209/07* (2013.01); *G06K 9/0014* (2013.01); *G06F 19/20* (2013.01)
USPC ............. 382/129; 382/128; 382/199; 702/19; 702/20

(58) Field of Classification Search
USPC ......... 382/128–133, 173–175, 199, 282–284; 435/4, 6.1; 600/352, 447, 476, 407; 702/19, 20, 27, 47
See application file for complete search history.

(56) References Cited

U.S. PATENT DOCUMENTS

| | | | |
|---|---|---|---|
| 4,410,799 A | 10/1983 | Okamoto |
| 4,758,727 A | 7/1988 | Tomei et al. |
| 4,766,381 A | 8/1988 | Conturo et al. |
| 4,855,597 A | 8/1989 | Shimura |
| 4,877,966 A | 10/1989 | Tomei et al. |
| 5,032,720 A | 7/1991 | White |
| 5,121,138 A | 6/1992 | Schermer et al. |

(Continued)

FOREIGN PATENT DOCUMENTS

| EP | 1186673 | 3/2002 |
|---|---|---|
| EP | 1162572 | 3/2006 |

(Continued)

OTHER PUBLICATIONS

Fang et al., "A Model-Based Analysis of Microarray Experimental Error and Normalisation," Nucleic Acids Research (2003) vol. 31, No. 16, pp. e96.*

(Continued)

*Primary Examiner* — Chan Park
*Assistant Examiner* — Mia M Thomas
(74) *Attorney, Agent, or Firm* — Banner & Witcoff, Ltd.

(57) ABSTRACT

The invention provides methods and systems for reconstructing feature intensities from pixel level data. In certain embodiments, the invention uses an empirically determined transfer function to construct a theoretical estimate of pixel level data and then iteratively updates feature intensities based on a minimum multiplicative error between the pixel level data and the theoretical estimate of the pixel level data.

20 Claims, 11 Drawing Sheets

(56) References Cited

U.S. PATENT DOCUMENTS

| | | |
|---|---|---|
| 5,143,854 A | 9/1992 | Pirrung et al. |
| 5,260,578 A | 11/1993 | Bliton et al. |
| 5,274,240 A | 12/1993 | Mathies et al. |
| 5,302,824 A | 4/1994 | Prager |
| 5,371,361 A | 12/1994 | Arends et al. |
| 5,485,530 A | 1/1996 | Lakowicz et al. |
| 5,528,050 A | 6/1996 | Miller et al. |
| 5,538,613 A | 7/1996 | Brumley et al. |
| 5,556,749 A | 9/1996 | Mitsuhashi et al. |
| 5,560,360 A | 10/1996 | Filler et al. |
| 5,578,832 A | 11/1996 | Trulson et al. |
| 5,631,734 A | 5/1997 | Stern et al. |
| 5,632,282 A | 5/1997 | Hay et al. |
| 5,689,110 A | 11/1997 | Dietz et al. |
| 5,754,676 A * | 5/1998 | Komiya et al. ............... 382/132 |
| 5,834,758 A | 11/1998 | Trulson et al. |
| 5,895,915 A | 4/1999 | DeWeerd et al. |
| 5,936,324 A | 8/1999 | Montagu |
| 5,981,956 A | 11/1999 | Stern |
| 5,984,474 A | 11/1999 | Schweitzer et al. |
| 6,025,601 A | 2/2000 | Trulson et al. |
| 6,064,754 A | 5/2000 | Parekh et al. |
| 6,075,613 A | 6/2000 | Schermer et al. |
| 6,078,390 A | 6/2000 | Bengtsson |
| 6,090,555 A * | 7/2000 | Fiekowsky et al. .......... 435/6.14 |
| 6,097,025 A | 8/2000 | Modlin et al. |
| 6,130,440 A | 10/2000 | Ogura |
| 6,141,096 A | 10/2000 | Stern et al. |
| 6,166,385 A | 12/2000 | Webb et al. |
| 6,169,289 B1 | 1/2001 | White et al. |
| 6,171,793 B1 | 1/2001 | Phillips et al. |
| 6,185,030 B1 | 2/2001 | Overbeck |
| 6,201,639 B1 | 3/2001 | Overbeck |
| 6,207,960 B1 | 3/2001 | Stern |
| 6,209,983 B1 | 4/2001 | Osborne et al. |
| 6,211,913 B1 | 4/2001 | Hansen et al. |
| 6,211,989 B1 | 4/2001 | Wulf et al. |
| 6,218,803 B1 | 4/2001 | Montagu et al. |
| 6,225,625 B1 | 5/2001 | Pirrung et al. |
| 6,229,607 B1 | 5/2001 | Shirai et al. |
| 6,239,782 B1 | 5/2001 | Siegel |
| 6,245,507 B1 | 6/2001 | Bogdanov |
| 6,278,435 B1 | 8/2001 | Etheridge et al. |
| 6,278,794 B1 | 8/2001 | Parekh et al. |
| 6,301,550 B1 | 10/2001 | Okamoto et al. |
| 6,309,601 B1 | 10/2001 | Juncosa et al. |
| 6,312,914 B1 | 11/2001 | Kardos et al. |
| 6,349,144 B1 | 2/2002 | Shams |
| 6,353,475 B1 | 3/2002 | Jensen et al. |
| 6,415,047 B1 | 7/2002 | Terry et al. |
| 6,420,108 B2 | 7/2002 | Mack et al. |
| 6,480,618 B1 | 11/2002 | Parekh et al. |
| 6,490,533 B2 | 12/2002 | Weiner et al. |
| 6,498,863 B1 | 12/2002 | Gaidoukevitch et al. |
| 6,510,391 B2 | 1/2003 | Balaban |
| 6,586,750 B2 | 7/2003 | Montagu |
| 6,591,196 B1 | 7/2003 | Yakhini et al. |
| 6,611,767 B1 | 8/2003 | Fiekowsky et al. |
| 6,621,929 B1 | 9/2003 | Lai et al. |
| 6,643,015 B2 | 11/2003 | Weiner |
| 6,650,411 B2 | 11/2003 | Odoy et al. |
| 6,674,882 B1 | 1/2004 | Shams |
| 6,731,781 B1 | 5/2004 | Shams et al. |
| 6,768,820 B1 | 7/2004 | Yakhini et al. |
| 6,778,692 B1 | 8/2004 | Yazici |
| 6,813,567 B2 | 11/2004 | Weiner et al. |
| 6,829,376 B2 | 12/2004 | Bartell |
| 6,954,699 B2 * | 10/2005 | Jevons et al. .................. 702/19 |
| 6,963,806 B2 * | 11/2005 | Gulati ............................. 702/20 |
| 6,965,704 B2 | 11/2005 | Kaushikkar et al. |
| 6,990,221 B2 | 1/2006 | Shams |
| 6,993,173 B2 * | 1/2006 | Zuzan et al. .................. 382/129 |
| 6,996,475 B2 | 2/2006 | Balaban |
| 7,006,680 B2 | 2/2006 | Gulati |
| 7,006,927 B2 | 2/2006 | Yakhini et al. |
| 7,027,629 B2 | 4/2006 | Cattell et al. |
| 7,031,844 B2 | 4/2006 | Bozinov et al. |
| 7,062,092 B2 * | 6/2006 | Kaushikkar et al. .......... 382/213 |
| 7,079,140 B2 * | 7/2006 | Boehler et al. ................. 345/440 |
| 7,116,809 B2 | 10/2006 | Bartell |
| 7,130,458 B2 | 10/2006 | Bartell |
| 7,184,610 B2 | 2/2007 | Weinstein |
| 7,217,573 B1 | 5/2007 | Oshida et al. |
| 7,222,025 B2 | 5/2007 | Weiner et al. |
| 7,317,820 B2 | 1/2008 | Park |
| 7,466,851 B2 | 12/2008 | Gulati |
| 7,498,176 B2 | 3/2009 | McCormick et al. |
| 7,636,636 B2 | 12/2009 | Piper |
| 7,920,908 B2 | 4/2011 | Hattery et al. |
| 8,009,889 B2 | 8/2011 | Hubbell |
| 8,094,119 B2 * | 1/2012 | Nonaka et al. ................. 345/102 |
| 8,284,243 B2 * | 10/2012 | Lee et al. ........................ 348/59 |
| 8,334,952 B2 * | 12/2012 | Wu et al. ....................... 349/112 |
| 8,369,596 B2 * | 2/2013 | Hubbell ......................... 382/129 |
| 2002/0028521 A1 | 3/2002 | Ogura |
| 2002/0049544 A1 | 4/2002 | Nislow et al. |
| 2002/0097912 A1 | 7/2002 | Kimmel et al. |
| 2002/0102564 A1 | 8/2002 | Mittmann et al. |
| 2002/0106117 A1* | 8/2002 | Bartell et al. ................. 382/129 |
| 2002/0150935 A1 | 10/2002 | Zhou et al. |
| 2002/0183606 A1* | 12/2002 | Boehler et al. ................ 600/407 |
| 2003/0038812 A1 | 2/2003 | Bartell |
| 2003/0087289 A1* | 5/2003 | Zuzan et al. ..................... 435/6 |
| 2003/0148286 A1 | 8/2003 | Larose et al. |
| 2003/0152490 A1 | 8/2003 | Trulson |
| 2003/0157545 A1 | 8/2003 | Jevons et al. |
| 2004/0006431 A1 | 1/2004 | Bartell |
| 2004/0019433 A1 | 1/2004 | Carpaij |
| 2004/0033485 A1* | 2/2004 | Li et al. ............................ 435/4 |
| 2004/0063136 A1 | 4/2004 | Gulati ............................... 435/6 |
| 2004/0096854 A1 | 5/2004 | Choong |
| 2004/0101846 A1 | 5/2004 | Collins et al. |
| 2004/0132080 A1* | 7/2004 | Kawaguchi et al. ............. 435/6 |
| 2004/0220897 A1 | 11/2004 | Bernhart et al. |
| 2004/0224332 A1 | 11/2004 | Loney |
| 2005/0153356 A1* | 7/2005 | Okawa et al. .................... 435/6 |
| 2005/0216201 A1 | 9/2005 | Hubbell et al. |
| 2005/0221351 A1 | 10/2005 | Ryu |
| 2005/0239113 A1 | 10/2005 | Ryu |
| 2005/0239114 A1 | 10/2005 | Ryu |
| 2005/0239115 A1 | 10/2005 | Ryu |
| 2005/0260507 A1 | 11/2005 | Mittmann et al. |
| 2005/0273011 A1* | 12/2005 | Hattery et al. ................. 600/476 |
| 2006/0074563 A1 | 4/2006 | Jevons et al. |
| 2006/0094040 A1 | 5/2006 | Hubbell et al. |
| 2006/0142951 A1 | 6/2006 | Balaban |
| 2006/0173634 A1 | 8/2006 | Ben-Dor et al. |
| 2006/0177116 A1 | 8/2006 | Cattell et al. |
| 2006/0184038 A1 | 8/2006 | Smith et al. |
| 2006/0200321 A1 | 9/2006 | Hubbell |
| 2006/0229824 A1 | 10/2006 | Cronin et al. |
| 2006/0241868 A1 | 10/2006 | Sun et al. |
| 2006/0281991 A1 | 12/2006 | Fitzpatrick et al. |
| 2006/0293860 A1 | 12/2006 | Bressler et al. |
| 2007/0054286 A1 | 3/2007 | Cronin et al. |
| 2007/0064990 A1 | 3/2007 | Roth |
| 2007/0149866 A1 | 6/2007 | Draayer et al. |
| 2007/0238954 A1 | 10/2007 | White et al. |
| 2007/0263914 A1* | 11/2007 | Tibbetts ........................ 382/129 |
| 2008/0031536 A1 | 2/2008 | Liao et al. |
| 2008/0232657 A1 | 9/2008 | Hubbell |
| 2009/0092227 A1 | 4/2009 | David et al. |
| 2010/0110103 A1 | 5/2010 | Ramirez et al. |
| 2011/0274328 A1 | 11/2011 | Hubbell |

FOREIGN PATENT DOCUMENTS

| | | |
|---|---|---|
| WO | WO 98/35223 | 8/1998 |
| WO | WO 99/47964 | 9/1999 |
| WO | WO 01/56216 | 8/2001 |
| WO | WO 03/030620 | 4/2003 |
| WO | WO 03/033128 | 4/2003 |

(56) References Cited

FOREIGN PATENT DOCUMENTS

| WO | WO 03/033741 | 4/2003 |
|---|---|---|
| WO | WO 03/034064 | 4/2003 |

OTHER PUBLICATIONS

Aleskerov et al. "Utility representation via addictive or multiplicative error functions", Discrete Applied Mathematics 127 (2003), pp. 181-197.

de Boer, "Empirical Speckle Transfer Function Measurements from Partial Eclipse Observations of the Sun Astronomy & Astrophysics Supplement Series", Dec. 1, 1995, pp. 1-6.

Fuhrman et al., "The Application of Shannon Entropy in the Identification of Putative Drug Targets," BioSystems 55, pp. 5-14 (2000).

Gullans, "Of Microarrays and Meandering Data Points," Nature Genetics, vol. 26, No. 1, pp. 4-5 (2000).

Huber et al. "Bioconductor Project Working Papers" Deparment of Molecular Genome Analysis, German Cancer Research Center, 2004, pp. 1-9.

Lekkas et al. "Improved non-linear transfer function and NN methods of flow routing for real time forecasting", Journal of Hydrodynamics IWA Publishing 2001, pp. 1-12 (153-164).

Li et al., "Model-based analysis of oligonucleotide arrays: Expression index computation and outlier detection," PNAS, vol. 98, No. 1, pp. 31-36 (Jan. 2001).

Marques T. "Predicting and Correcting Bias Caused by Measurement Error in Line Transect using Mutiplicative Error Models", Biometrics 60, pp. 757-763, Sep. 2004.

Montagu and Weiner, "Fluorescence Array Scanner Employing a Flying Objective," Journal of the Association for Laboratory Automation, vol. 4, No. 1, pp. 40-43 (Mar. 1999).

Schuchhardt et al., "Normalization strategies for cDNA Microarrays," Nucleic Acids Research, vol. 28, No. 10, e47 (2000).

Tseng et al., "Issues in cDNA Microarray Analysis: Quality Filtering, Channel Normalization, Models of Variations and Assessment of Gene Effects," Nucleic Acids Research, vol. 29, No. 12, pp. 2549-2557 (2001).

Zhao et al, "Digital Radiology using Active Matrix Readout of Amorphous Selenium", American Association of Physicists in Medicine (1997) pp. 1-10.

Zuzan, "Estimating probe cell locations," Institute of Statistics and Decision Sciences, Duke University, Nov. 19, 2001, Affymetrix, Inc. Data Analysis Workshop.

\* cited by examiner

US 8,934,689 B2

FEATURE INTENSITY RECONSTRUCTION OF BIOLOGICAL PROBE ARRAY

RELATED APPLICATIONS

This application is a continuation of U.S. patent application Ser. No. 11/769,600 filed Jun. 27, 2007, which claims the benefit of U.S. Provisional Application No. 60/817,126 filed Jun. 27, 2006. The entire disclosure of the above applications is incorporated herein by reference in their entirety for all purposes.

FIELD OF INVENTION

The present invention relates to the field of image processing. More specifically, the present invention relates to a method of modifying feature intensity from image data of a feature in a biological array.

BACKGROUND OF THE INVENTION

Devices and computer systems for forming and using arrays of materials on a chip or substrate are known. For example, PCT applications WO92/10588 and 95/11995, both incorporated herein by reference for all purposes, describe techniques for sequencing or sequence checking nucleic acids and other materials. Arrays for performing these operations may be formed according to the methods of, for example, the techniques disclosed in U.S. Pat. Nos. 5,445,934, 5,384,261 and 5,571,639, each incorporated herein by reference for all purposes.

According to one aspect of the techniques described therein, an array of nucleic acid probes is fabricated at known or determinable locations on a solid support, such as a chip. A nucleic acid is then brought into contact with the solid support to allow hybridization between the probes on the array and targets in the nucleic acid, the hybridization of the target results in association with a detectable label at the location of the probe, for example, the target may carry a label or the probe or target may be labeled as a result of hybridization of the target to the probe, for example, the probe may be extended with a labeled nucleotide or nucleotides using the target as a template. A scanner generates an image file (also called a .cel file) indicating the locations where the nucleic acids are bound to the chip. Based upon the image file and identities of the probes at specific locations, it becomes possible to extract information such as the nucleotide or monomer sequence of the bound DNA or RNA. Such systems have been used to form, for example, arrays of DNA that may be used to study and detect mutations relevant to genetic diseases, cancers, infectious diseases, HIV, and other genetic characteristics.

For sequence checking applications, the chip may be "tiled" for a specific target nucleic acid sequence. As an example, the chip may contain probes that are perfectly complementary to the target sequence and probes that differ from the target sequence by a single base mismatch. For de novo sequencing applications, the chip may include all the possible probes of a specific length. The probes are tiled on a chip in rows and columns of cells, where each cell includes multiple copies of a particular probe. Additionally, "blank" cells may be present on the chip which do not include any probes. As the blank cells contain no probes, labeled targets should not bind specifically to the chip in this area. Thus, a blank cell provides a measure of the background intensity.

Labeled targets in hybridized probe-target pairs may be detected using various commercial devices, referred to for convenience hereafter as scanners. Scanners image the targets by detecting fluorescent or other emissions from the labels. Data representing the detected emissions are stored in a memory device for processing. The processed images may be presented to a user on a video monitor or other device, and/or operated upon by various data processing products or systems. Some techniques are known for identifying the data representing detected emissions and separating them from background information. For example, U.S. Pat. No. 6,090,555 to Fiekowsky, et al. describes various of these techniques.

In the scanned image file, a cell is typically represented by multiple pixels. Although a visual inspection of the scanned image file may be performed to identify the individual cells in the scanned image file, it would be desirable to utilize computer-implemented image processing techniques to align the scanned image file.

Accordingly, there is a need for a system and method suitable for storing and organizing large quantities of information used in conjunction with probe arrays.

SUMMARY OF THE INVENTION

This invention provides methods, computer software products and systems for the method of reconstructing feature intensities robustly from pixel level data of each feature under an approximate error model. The reconstruction utilizes minimal assumptions involving linearity of intensity and shape of feature.

The present invention relates to a method of modifying feature intensity from image data of a feature in a biological array comprising obtaining one or more sample image data of a feature from a biological probe array, determining a theoretical pixel intensity with a transfer function representing the proportion of the intensity in a set of pixels due to a feature, a feature intensity of said feature, and a background value of said feature, wherein the theoretical pixel intensity equals the value of a set of observed pixels of said feature, determining an optimized multiplicative error function wherein said multiplicative error function comprises said theoretical pixel intensity and said set of observed pixels value, and determining said feature intensity with an update rule for said feature intensity using a weight function representing the weight of said pixel and the optimized multiplicative error function, wherein said update rule for said feature intensity will iteratively generate a unique a value to which said feature intensity converges.

The present invention is directed to a method for modifying feature intensity from image data at pixel level of a biological array. Generally speaking, this method seeks a modification of feature intensity robustly from pixel level data to provide a singular feature value. It is well known that the intensity profiles of features look less uniform over the area making up the feature as feature size is reduced. For example, at 11 μm feature pitch and 8 μm square active area, intensities vary around a central plateau. At 5 μm feature pitch and 3 μm feature active area a small zone of peak intensity is present at the center of the feature however intensities fall as the edge of the feature is approached. If the pixel size is not changed, then as the feature size becomes smaller, fewer pixels would represent the smaller feature. According to the invention, feature intensity is robustly determined from the pixel level data under an approximately multiplicative error model. This depends upon minimal assumptions involving linearity of intensity and shape of feature.

Usually an image includes image features made up of pixels. For example, the image may include a checkerboard pattern in which the image features are alternating bright and dim squares. Each of the squares is made up of a number of pixels. It will be understood, however, that the pattern is not limited to a checkerboard, and that the image features may be any shape or combination of shapes.

The method includes the step of (a) obtaining one or more sample image data of a feature from a biological probe array. This step involves obtaining a scanned image of the feature where the scanned image is comprised of pixel data. Depending on the size of the feature or the power of the scanner, the number of pixels in the feature varies.

The next step in the method is (b) determining a theoretical pixel intensity with a transfer function representing the proportion of the intensity in a set of pixels due to a feature and a feature intensity of the feature and a background value of the feature, wherein the theoretical pixel intensity equals the value of a set of observed pixels of the feature. Here the feature intensity is unknown, the transfer function is predetermined, and the background can be initialized as the lowest observed pixel intensity larger than zero.

This is followed by (c) determining an optimized multiplicative error function with a multiplicative error function and a standard deviation function wherein the multiplicative error function comprises the theoretical pixel intensity and the set of observed pixels value. The multiplicative error function represents the multiplicative error of observed intensity of a pixel on the feature. The intensity of hybridization of a DNA spot on a microarray is often used as measure of gene expression, but the raw intensity is subject to a number of confounding error terms, such as DNA concentration in a spot and sequence hybridization efficiency. These error terms may be modeled multiplicatively. The standard deviation function is used to truncate the outliers, e.g., so the application can be run more efficiently.

The final step is (d) determining the feature intensity with an update rule for the feature intensity using a weight function representing the weight of the pixel and the optimized multiplicative error function, wherein the update rule for the feature intensity will iteratively generate a unique a value to which the feature intensity converges. The weight function of the pixel adjusts a numeric value proportional to the importance of a pixel (pixel weight) so that pixels near the border or mis-synthesized pixels have a low weight and pixels near the center of the feature have a high weight. By running the update rule iteratively, assuming transfer function and background value is fixed, the feature intensity will have a unique value to which it converges.

In some embodiments, the update rule for a transfer function can be determined using the same algorithm where the background value, observed pixel value and the feature intensity are provided.

In some other embodiments, the weight function applied in the update rule for a transfer function will be limited to only 10 pixels.

In other embodiments, the center of the feature is updated as an iterative step within the model by choosing the center that best fits the data for feature extraction. Still in other embodiments, the background can be initialized as the lowest observed pixel intensity larger than zero.

The invention is directed in yet further embodiments to a computer program product for modifying feature intensity from image data of a feature. The computer program product typically is embodied in a computer-readable medium, such as a CD-ROM, a disk, or in internal RAM or other memory. Moreover, the product may be implemented in other forms, such as hardware or a combination of hardware and software.

In another embodiment, the invention is directed to a computer system for modifying feature intensity from image data of a feature. The computer system includes a computer program product for modifying feature intensity from image data of a feature.

In yet another embodiment, the invention is directed to a computer-readable medium, such as a CD-ROM, a disk, or in internal RAM or other memory storing the computer-executable instructions for performing the method for modifying feature intensity from image data of a feature (e.g., for a) obtaining one or more sample image data of a feature from a biological probe array; b) determining a weighted observed intensity of a pixel by modifying an observed intensity of the pixel on the feature with a weight function representing an expected importance of the pixel on the feature and a multiplicative error function representing a multiplicative error of the observed intensity of the pixel on the feature; c) defining a transfer function to be a proportion of intensity of the pixel due to the feature and a distance of the pixel from the feature center; d) determining a value of a feature intensity of the feature using the transfer function and the weighted observed intensity of the pixel and a background intensity of the feature, wherein the weighted observed intensity value of the pixel is iteratively updated to converge on the value of the said feature intensity.)

Figure 1:
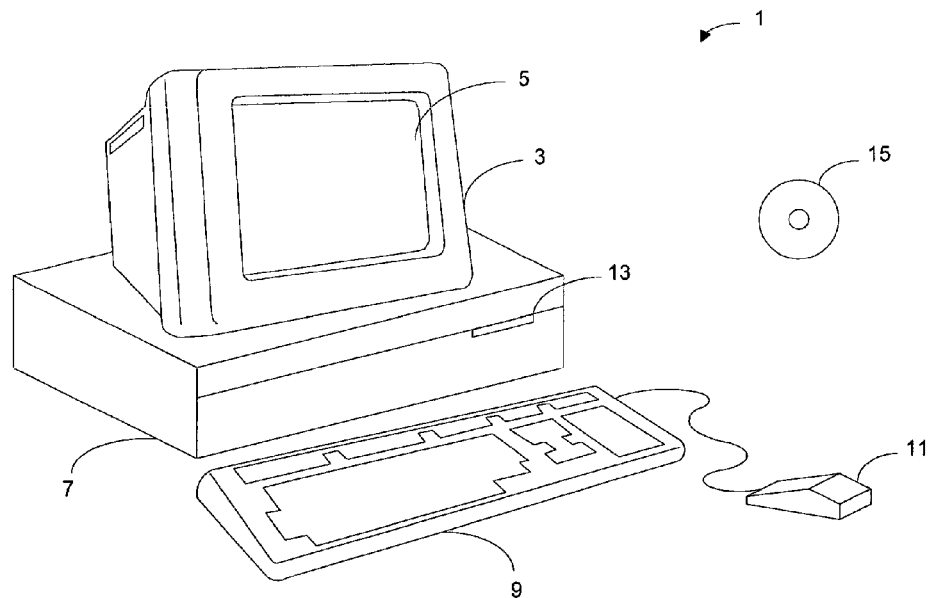
FIG. 1 illustrates an example of a computer system that may be utilized to execute the software of an embodiment of the invention.

DETAILED DESCRIPTION OF THE INVENTION a) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being, but may also be other organisms including, but not limited to, mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual*, *Cells: A Laboratory Manual*, *PCR Primer: A Laboratory Manual*, and *Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, *IRL Press, London*, Nelson and Cox (2000), Lehninger, *Principles of Biochemistry* $3^{rd}$ Ed., W.H. Freeman Pub., New York, N.Y. and Berg et al. (2002) *Biochemistry*, $5^{th}$ Ed., W.H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S. Ser. Nos. 09/536,841 and 10/730,771 (U.S. Patent Publication No. 2005-0074787), WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication No. WO 99/36760) and PCT/US01/04285 (International Publication No. WO 01/58593), which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are described, for example, in U.S. Patent Publication No. 20070016382, which describes genotyping arrays for selected panels of SNPs and U.S. Patent Publication No. 20070054286.

The present invention also contemplates many uses for polymers attached to solid substrates. These uses include gene expression monitoring, profiling, library screening, genotyping and diagnostics. Gene expression monitoring and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Ser. No. 10/442,021 (U.S. Patent Publication No. 20070065816), Ser. No. 10/013,598 (U.S. Patent Application Publication 20030036069), and U.S. Pat. Nos. 5,856,092, 6,300,063, 5,858,659, 6,284,460, 6,361,947, 6,368,799 and 6,333,179. Other uses are embodied in U.S. Pat. Nos. 5,871,928, 5,902,723, 6,045,996, 5,541,061, and 6,197,506.

The present invention also contemplates sample preparation methods in certain preferred embodiments. Prior to or concurrent with analysis, the genomic sample may be amplified by a variety of mechanisms, some of which may employ PCR. See, for example, *PCR Technology: Principles and Applications for DNA Amplification* (Ed. H. A. Erlich, Freeman Press, NY, N.Y., 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159, 4,965,188, and 5,333,675, each of which is incorporated herein by reference in their entireties for all purposes. The sample may be amplified on the array. See, for example, U.S. Pat. No. 6,300,070 and U.S. Ser. No. 09/513,300, which are incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci. USA* 86, 1173 (1989) and WO88/10315), self-sustained sequence replication (Guatelli et al., *Proc. Nat. Acad. Sci. USA*, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NABSA). (See, U.S. Pat. Nos. 5,409,818, 5,554,517, and 6,063,603, each of which is incorporated herein by reference). Other amplification methods that may be used are described in U.S. Pat. Nos. 5,242,794, 5,494,810, 4,988,617 and 6,582,938, each of which is incorporated herein by reference.

Additional methods of sample preparation and techniques for reducing the complexity of a nucleic sample are described in Dong et al., *Genome Research* 11, 1418 (2001), in U.S. Pat. Nos. 6,361,947, 6,391,592 and 6,872,529 and U.S. Ser. Nos. 09/916,135, 09/920,491 (U.S. Patent Application Publication 20030096235), and Ser. No. 09/910,292 (U.S. Patent Application Publication 20030082543).

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* (2nd Ed. Cold Spring Harbor, N.Y. 1989); Berger and Kimmel *Methods in Enzymology*, Vol. 152, *Guide to Molecular Cloning Techniques* (Academic Press, Inc., San Diego, Calif., 1987); Young and Davis, *P.N.A.S,* 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred embodiments. See U.S. Pat. Nos. 5,143,854, 5,578,832, 5,631,734, 5,834,758, 5,936,324, 5,981,956, 6,025,601, 6,141,096, 6,185,030, 6,201,639, 6,218,803, and 6,225,625 in U.S. Ser. No. 10/389,194 (U.S. Patent Publication No. 20040012676) and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758, 5,856,092, 5,902,723, 5,936,324, 5,981,956, 6,025,601, 6,090,555, 6,141,096, 6,185,030, 6,201,639; 6,218,803; and 6,225,625, in U.S. Ser. No. 10/389,194 (U.S. Patent Publication No. 20040012676), 60/493,495, and U.S. Patent Publication No. 20050059062 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes, etc. The computer-executable instructions may be written in a suitable computer language or combination of several languages. Basic computational biology methods are described in, for example, Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., 2nd ed., 2001). See U.S. Pat. No. 6,420,108.

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. The present invention may also make use of computer program products and software for analysis of array data, for example, U.S. Patent Publication Nos. 20050118627 and 20030003450 relating to gene expression analysis using linear programming and U.S. Patent Publication 20060142951

Additionally, the present invention may have preferred embodiments that include methods for providing genetic information over networks such as the Internet as shown in U.S. Ser. Nos. 10/197,621, 10/063,559 (United States Publication No. 20020183936), Ser. No. 10/065,856 (U.S. Patent Publication No. 20030100995), Ser. No. 10/065,868 (U.S. Patent Publication No. 20030120432), Ser. No. 10/328,818 (U.S. Patent Publication No. 2004-0002818), Ser. No. 10/328,872 (U.S. Patent Publication No. 2004-0126840), Ser. No. 10/423,403 (U.S. Patent Publication No. 2004-0049354), and 60/482,389.

b) Definitions

The term "array" as used herein refers to an intentionally created collection of molecules which can be prepared either synthetically or biosynthetically. The molecules in the array can be identical or different from each other. The array can assume a variety of formats, for example, libraries of soluble molecules; libraries of compounds tethered to resin beads, silica chips, or other solid supports.

The term "complementary" as used herein refers to the hybridization or base pairing between nucleotides or nucleic acids, such as, for instance, between the two strands of a double stranded DNA molecule or between an oligonucleotide primer and a primer binding site on a single stranded nucleic acid to be sequenced or amplified. Complementary nucleotides are, generally, A and T (or A and U), or C and G. Two single stranded RNA or DNA molecules are said to be complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

The term "excitation energy" as used herein refers to energy used to energize a detectable label for detection, for example illuminating a fluorescent label. Devices for this use include coherent light or non coherent light, such as lasers, UV light, light emitting diodes, an incandescent light source, or any other light or other electromagnetic source of energy having a wavelength in the excitation band of an excitable label, or capable of providing detectable transmitted, reflective, or diffused radiation.

The term "genome" as used herein is all the genetic material in the chromosomes of an organism. DNA derived from the genetic material in the chromosomes of a particular organism is genomic DNA. A genomic library is a collection of clones made from a set of randomly generated overlapping DNA fragments representing the entire genome of an organism.

The term "hybridization" as used herein refers to the process in which two single-stranded polynucleotides bind non-covalently to form a stable double-stranded polynucleotide; triple-stranded hybridization is also theoretically possible. The resulting (usually) double-stranded polynucleotide is a "hybrid." The proportion of the population of polynucleotides that forms stable hybrids is referred to herein as the "degree of hybridization." Hybridizations are usually performed under stringent conditions, for example, at a salt concentration of no more than 1M and a temperature of at least 25° C. For example, conditions of 5×SSPE (750 mM NaCl, 50 mM NaPhosphate, 5 mM EDTA, pH 7.4) and a temperature of 25-30° C. are suitable for allele-specific probe hybridizations. For stringent conditions, see, for example, Sambrook, Fritsche and Maniatis. "Molecular Cloning A laboratory Manual" 2nd Ed. Cold Spring Harbor Press (1989) which is hereby incorporated by reference in its entirety for all purposes above.

The term "hybridization conditions" as used herein will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

The term "hybridization probes" as used herein are oligonucleotides capable of binding in a base-specific manner to a complementary strand of nucleic acid. Such probes include peptide nucleic acids, as described in Nielsen et al., *Science* 254, 1497-1500 (1991), and other nucleic acid analogs and nucleic acid mimetics.

The term "label" as used herein refers to a luminescent label, a light scattering label or a radioactive label. Fluorescent labels include, inter alia, the commercially available fluorescein phosphoramidites such as Fluoreprime (Pharmacia), Fluoredite (Millipore) and FAM (ABI). See U.S. Pat. No. 6,287,778.

The term "ligand" as used herein refers to a molecule that is recognized by a particular receptor. The agent bound by or reacting with a receptor is called a "ligand," a term which is definitionally meaningful only in terms of its counterpart receptor. The term "ligand" does not imply any particular molecular size or other structural or compositional feature other than that the substance in question is capable of binding or otherwise interacting with the receptor. Also, a ligand may serve either as the natural ligand to which the receptor binds, or as a functional analogue that may act as an agonist or antagonist. Examples of ligands that can be investigated by this invention include, but are not restricted to, agonists and antagonists for cell membrane receptors, toxins and venoms, viral epitopes, hormones (for example, opiates, steroids, etc.), hormone receptors, peptides, enzymes, enzyme substrates, substrate analogs, transition state analogs, cofactors, drugs, proteins, and antibodies.

The term "microtiter plates" as used herein refers to arrays of discrete wells that come in standard formats (96, 384 and 1536 wells) which are used for examination of the physical, chemical or biological characteristics of a quantity of samples in parallel.

The term "monomer" as used herein refers to any member of the set of molecules that can be joined together to form an oligomer or polymer. The set of monomers useful in the present invention includes, but is not restricted to, for the example of (poly)peptide synthesis, the set of L-amino acids, D-amino acids, or synthetic amino acids. As used herein, "monomer" refers to any member of a basis set for synthesis of an oligomer. For example, dimers of L-amino acids form a basis set of 400 "monomers" for synthesis of polypeptides. Different basis sets of monomers may be used at successive steps in the synthesis of a polymer. The term "monomer" also refers to a chemical subunit that can be combined with a different chemical subunit to form a compound larger than either subunit alone.

The term "nucleic acid library" or sometimes refer by "array" as used herein refers to an intentionally created collection of nucleic acids which can be prepared either synthetically or biosynthetically and screened for biological activity in a variety of different formats (for example, libraries of soluble molecules; and libraries of oligos tethered to resin beads, silica chips, or other solid supports). Additionally, the term "array" is meant to include those libraries of nucleic acids which can be prepared by spotting nucleic acids of essentially any length (for example, from 1 to about 1000 nucleotide monomers in length) onto a substrate. The term "nucleic acid" as used herein refers to a polymeric form of nucleotides of any length, either ribonucleotides, deoxyribonucleotides or peptide nucleic acids (PNAs), that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. Thus the terms nucleoside, nucleotide, deoxynucleoside and deoxynucleotide generally include analogs such as those described herein. These analogs are those molecules having some structural features in common with a naturally occurring nucleoside or nucleotide such that when incorporated into a nucleic acid or oligonucleoside sequence, they allow hybridization with a naturally occurring nucleic acid sequence in solution. Typically, these analogs are derived from naturally occurring nucleosides and nucleotides by replacing and/or modifying the base, the ribose or the phosphodiester moiety. The changes can be tailor made to stabilize or destabilize hybrid formation or enhance the specificity of hybridization with a complementary nucleic acid sequence as desired.

The term "nucleic acids" as used herein may include any polymer or oligomer of pyrimidine and purine bases, preferably cytosine, thymine, and uracil, and adenine and guanine, respectively. See Albert L. Lehninger, PRINCIPLES OF BIOCHEMISTRY, at 793-800 (Worth Pub. 1982). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

The term "oligonucleotide" or sometimes refer by "polynucleotide" as used herein refers to a nucleic acid ranging from at least 2, preferable at least 8, and more preferably at least 20 nucleotides in length or a compound that specifically hybridizes to a polynucleotide. Polynucleotides of the present invention include sequences of deoxyribonucleic acid (DNA) or ribonucleic acid (RNA) which may be isolated from natural sources, recombinantly produced or artificially synthesized and mimetics thereof. A further example of a polynucleotide of the present invention may be peptide nucleic acid (PNA). The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term "primer" as used herein refers to a single-stranded oligonucleotide capable of acting as a point of initiation for template-directed DNA synthesis under suitable conditions for example, buffer and temperature, in the presence of four different nucleoside triphosphates and an agent for polymerization, such as, for example, DNA or RNA polymerase or reverse transcriptase. The length of the primer, in any given case, depends on, for example, the intended use of the primer, and generally ranges from 15 to 30 nucleotides. Short primer molecules generally require cooler temperatures to form sufficiently stable hybrid complexes with the template. A primer need not reflect the exact sequence of the template but must be sufficiently complementary to hybridize with such template. The primer site is the area of the template to which a primer hybridizes. The primer pair is a set of primers including a 5' upstream primer that hybridizes with the 5' end of the sequence to be amplified and a 3' downstream primer that hybridizes with the complement of the 3' end of the sequence to be amplified.

The term "probe" as used herein refers to a surface-immobilized molecule that can be recognized by a particular target. See U.S. Pat. No. 6,582,908 for an example of arrays having all possible combinations of probes with 10, 12, and more bases. Examples of probes that can be investigated by this invention include, but are not restricted to, agonists and antagonists for cell membrane receptors, toxins and venoms, viral epitopes, hormones (for example, opioid peptides, steroids, etc.), hormone receptors, peptides, enzymes, enzyme substrates, cofactors, drugs, lectins, sugars, oligonucleotides, nucleic acids, oligosaccharides, proteins, and monoclonal antibodies.

The term "receptor" as used herein refers to a molecule that has an affinity for a given ligand. Receptors may be naturally-occurring or manmade molecules. Also, they can be employed in their unaltered state or as aggregates with other species. Receptors may be attached, covalently or noncovalently, to a binding member, either directly or via a specific binding substance. Examples of receptors which can be employed by this invention include, but are not restricted to, antibodies, cell membrane receptors, monoclonal antibodies and antisera reactive with specific antigenic determinants (such as on viruses, cells or other materials), drugs, polynucleotides, nucleic acids, peptides, cofactors, lectins, sugars, polysaccharides, cells, cellular membranes, and organelles. Receptors are sometimes referred to in the art as anti-ligands. As the term receptors is used herein, no difference in meaning is intended. A "Ligand Receptor Pair" is formed when two macromolecules have combined through molecular recognition to form a complex. Other examples of receptors which can be investigated by this invention include but are not restricted to those molecules shown in U.S. Pat. No. 5,143,854, which is hereby incorporated by reference in its entirety.

The term "solid support", "support", and "substrate" as used herein are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. See U.S. Pat. No. 5,744,305 for exemplary substrates.

The term "surface" or "active probe surface" or "target surface" as used herein refers to the area of the microarray to be analyzed with reagents.

The term "target" as used herein refers to a molecule that has an affinity for a given probe. Targets may be naturally-occurring or man-made molecules. Also, they can be employed in their unaltered state or as aggregates with other species. Targets may be attached, covalently or noncovalently, to a binding member, either directly or via a specific binding substance. Examples of targets which can be employed by this invention include, but are not restricted to, antibodies, cell membrane receptors, monoclonal antibodies and antisera reactive with specific antigenic determinants (such as on viruses, cells or other materials), drugs, oligonucleotides, nucleic acids, peptides, cofactors, lectins, sugars, polysaccharides, cells, cellular membranes, and organelles. Targets are sometimes referred to in the art as anti-probes. As the term targets is used herein, no difference in meaning is intended. A "Probe Target Pair" is formed when two macromolecules have combined through molecular recognition to form a complex.

The term "wafer" as used herein refers to a substrate having surface to which a plurality of arrays are bound. In a preferred embodiment, the arrays are synthesized on the surface of the substrate to create multiple arrays that are physically separate. In one preferred embodiment of a wafer, the arrays are physically separated by a distance of at least about 0.1, 0.25, 0.5, 1 or 1.5 millimeters. The arrays that are on the wafer may be identical, each one may be different, or there may be some combination thereof. Particularly preferred wafers are about 8"×8" and are made using the photolithographic process.

c). Overview

In the description that follows, the present invention will be described in reference to preferred embodiments that utilize VLSIPS™ technology for making very large arrays of oligonucleotide probes on chips. The VLSIPS™ technology provides methods of making very large arrays of oligonucleotide probes on very small chips. See U.S. Pat. No. 5,143,854 and PCT patent publication Nos. WO 90/15070 and 92/10092, each of which is incorporated by reference for all purposes. However, the invention is not limited to images produced in this fashion and may be advantageously applied to other hybridization technologies or images in other technology areas. Therefore, the description of the embodiments that follows is for purposes of illustration and not limitation.

FIG. 1 illustrates an example of a computer system that may be used to execute the software of an embodiment of the invention. FIG. 1 shows a computer system 1 that includes a display 3, screen 5, cabinet 7, keyboard 9, and mouse 11. Mouse 11 may have one or more buttons for interacting with a graphical user interface. Cabinet 7 houses a CD-ROM drive 13, system memory and a hard drive (see FIG. 2) which may be utilized to store and retrieve software programs incorporating computer code that implements the invention, data for use with the invention, and the like. Although a CD-ROM 15 is shown as an exemplary computer readable storage medium, other computer readable storage media including floppy disk, tape, flash memory, system memory, and hard drive may be utilized. Additionally, a data signal embodied in a carrier wave (e.g., in a network including the Internet) may be the computer readable storage medium.

Figure 2:
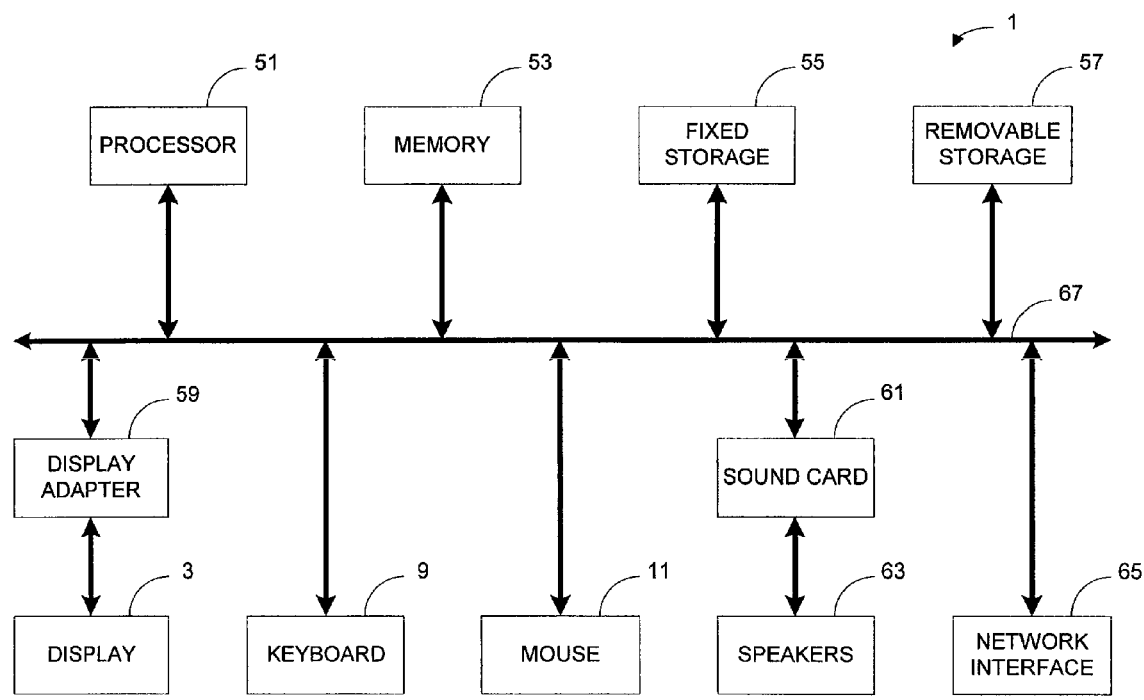
FIG. 2 illustrates a system block diagram of the computer system of FIG. 1.

FIG. 2 shows a system block diagram of computer system 1 used to execute the software of an embodiment of the invention. As in FIG. 1, computer system 1 includes monitor 3 and keyboard 9, and mouse 11. Computer system 1 further includes subsystems such as a central processor 51, system memory 53, fixed storage 55 (e.g., hard drive), removable storage 57 (e.g., CD-ROM drive), display adapter 59, sound card 61, speakers 63, and network interface 65. Other computer systems suitable for use with the invention may include additional or fewer subsystems. For example, another computer system could include more than one processor 51 (i.e., a multi-processor system) or a cache memory.

The system bus architecture of computer system 1 is represented by arrows 67. However, these arrows are illustrative of any interconnection scheme serving to link the subsystems. For example, a local bus could be utilized to connect the central processor to the system memory and display adapter. Computer system 1 shown in FIG. 2 is but an example of a computer system suitable for use with the invention. Other computer architectures having different configurations of subsystems may also be utilized.

The present invention provides methods of aligning scanned images or image files of hybridized arrays including nucleic acid probes. In a representative embodiment, the scanned image files include fluorescence data from a biological array, but the files may also represent other data such as radioactive intensity, light scattering, refractive index, conductivity, electroluminescence, or large molecule detection data. Therefore, the present invention is not limited to analyzing fluorescence measurements of hybridization but may be readily utilized to analyze other measurements of hybridization.

For purposes of illustration, the present invention is described as being part of a computer system that designs a chip mask, synthesizes the probes on the chip, labels the nucleic acids, and scans the hybridized nucleic acid probes. Such a system is fully described in U.S. Pat. No. 5,571,639, incorporated by reference for all purposes. However, the present invention may be used separately from the overall system for analyzing data generated by such systems.

Figure 3:
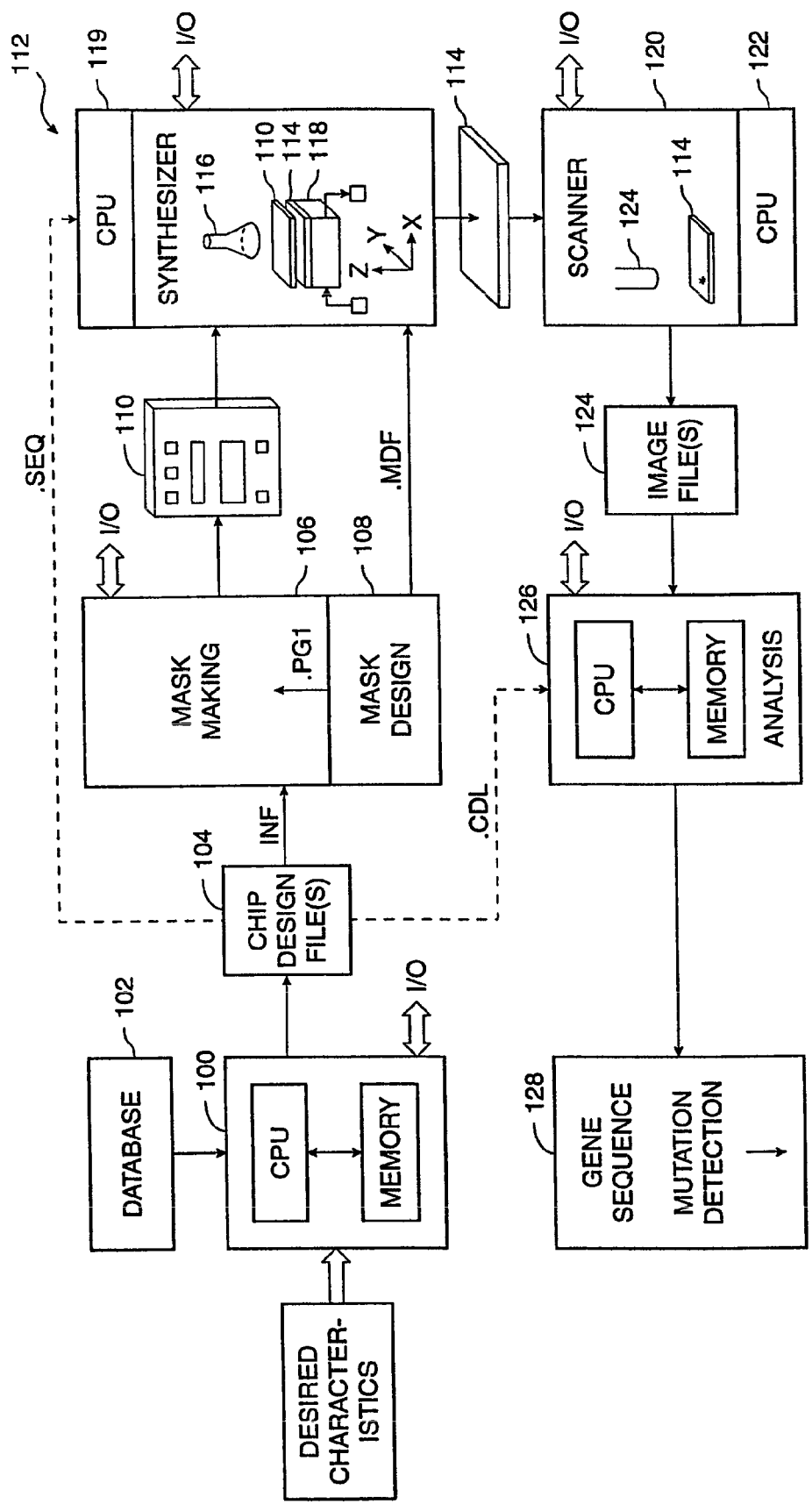
FIG. 3 illustrates an overall system for forming and analyzing arrays of biological materials such as DNA or RNA.
Figure 4:
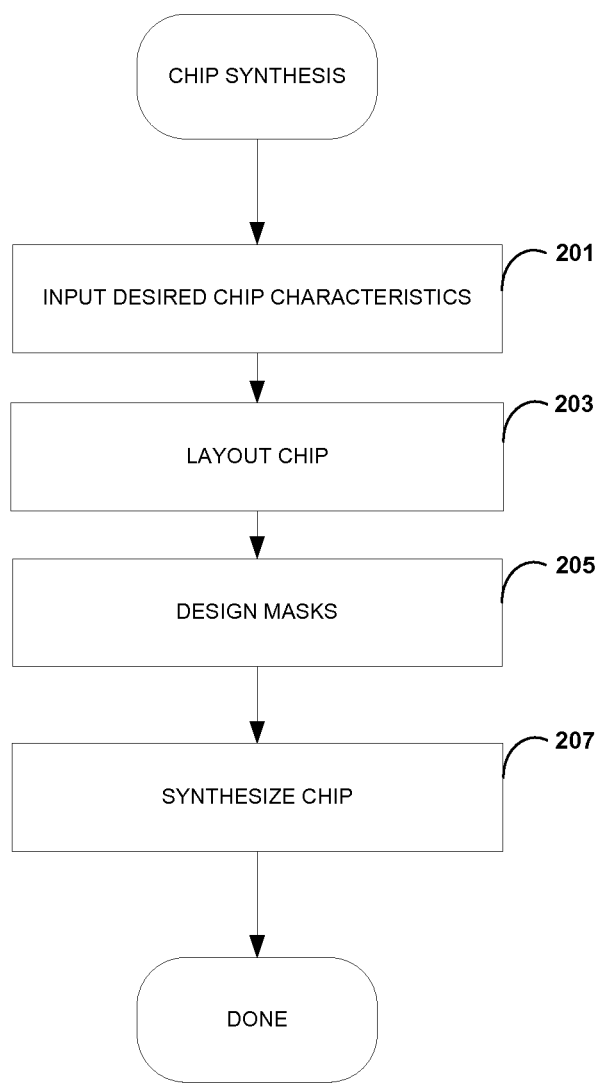
FIG. 4 is a high level flowchart of a process of synthesizing a chip.

FIG. 3 illustrates a computerized system for forming and analyzing arrays of biological materials such as RNA or DNA. A computer 100 is used to design arrays of biological polymers such as RNA and DNA. The computer 100 may be, for example, an appropriately programmed Sun Workstation or personal computer or workstation, such as an IBM PC equivalent, including appropriate memory and a CPU as shown in FIGS. 1 and 2. The computer system 100 obtains inputs from a user regarding characteristics of a gene of interest, and other inputs regarding the desired features of the array. Optionally, the computer system may obtain information regarding a specific genetic sequence of interest from an external or internal database 102 such as GenBank. The output of the computer system 100 is a set of chip design computer files 104 in the form of, for example, a switch matrix, as described in PCT application WO 92/10092, and other associated computer files.

The chip design files are provided to a system 106 that designs the lithographic masks used in the fabrication of arrays of molecules such as DNA. The system or process 106 may include the hardware necessary to manufacture masks 110 and also the necessary computer hardware and software 108 necessary to lay the mask patterns out on the mask in an efficient manner. As with the other features in FIG. 3, such equipment may or may not be located at the same physical site but is shown together for ease of illustration in FIG. 3. The system 106 generates masks 110 or other synthesis patterns such as chrome-on-glass masks for use in the fabrication of polymer arrays.

The masks 110, as well as selected information relating to the design of the chips from system 100, are used in a synthesis system 112. Synthesis system 112 includes the necessary hardware and software used to fabricate arrays of polymers on a substrate or chip 114. For example, synthesizer 112 includes a light source 116 and a chemical flow cell 118 on which the substrate or chip 114 is placed. Mask 110 is placed between the light source and the substrate/chip, and the two are translated relative to each other at appropriate times for deprotection of selected regions of the chip. Selected chemical regents are directed through flow cell 118 for coupling to the protected regions, as well as for washing and other operations. All operations are preferably directed by an appropriately programmed computer 119, which may or may not be the same computer as the computer(s) used in mask design and mask making.

The substrates fabricated by synthesis system 112 are optionally diced into smaller chips and exposed to marked targets. The targets may or may not be complementary to one or more of the molecules on the substrate. The targets are marked with a label such as a fluorescent label (indicated by an asterisk in FIG. 3) and placed in scanning system 120. Scanning system 120 again operates under the direction of an appropriately programmed digital computer 122, which also may or may not be the same computer as the computers used in synthesis, mask making, and mask design. The scanner 120 includes a detection device 124 such as a confocal microscope or CCD (charge-coupled device) that is used to detect the location where labeled target (*) has bound to the substrate. The output of scanner 120 is an image file(s) 124 indicating, in the case of fluorescent labeled target, the fluorescence intensity (photon counts or other related measurements, such as voltage) as a function of position on the substrate. Since higher photon counts will be observed where the labeled target has bound more strongly to the array of polymers (e.g., DNA probes on the substrate), and since the monomer sequence of the polymers on the substrate is known as a function of position, it becomes possible to determine the sequence(s) of polymer(s) on the substrate that are complementary to the target. Computer-aided techniques for monitoring gene expression using arrays of probes have also been developed as disclosed in EP Pub No. 0848067 and PCT publication No. WO 97/10365, the contents of which are herein incorporated by reference.

The image file 124 is provided as input to an analysis system 126 that incorporates the techniques of the present invention. Again, the analysis system may be any one of a wide variety of computer system(s), but in a preferred embodiment the analysis system is based on a WINDOWS NT workstation or equivalent. The analysis system may analyze the image file(s) to generate appropriate output 128, such as the identity of specific mutations in a target such as DNA or RNA.

Figure 5:
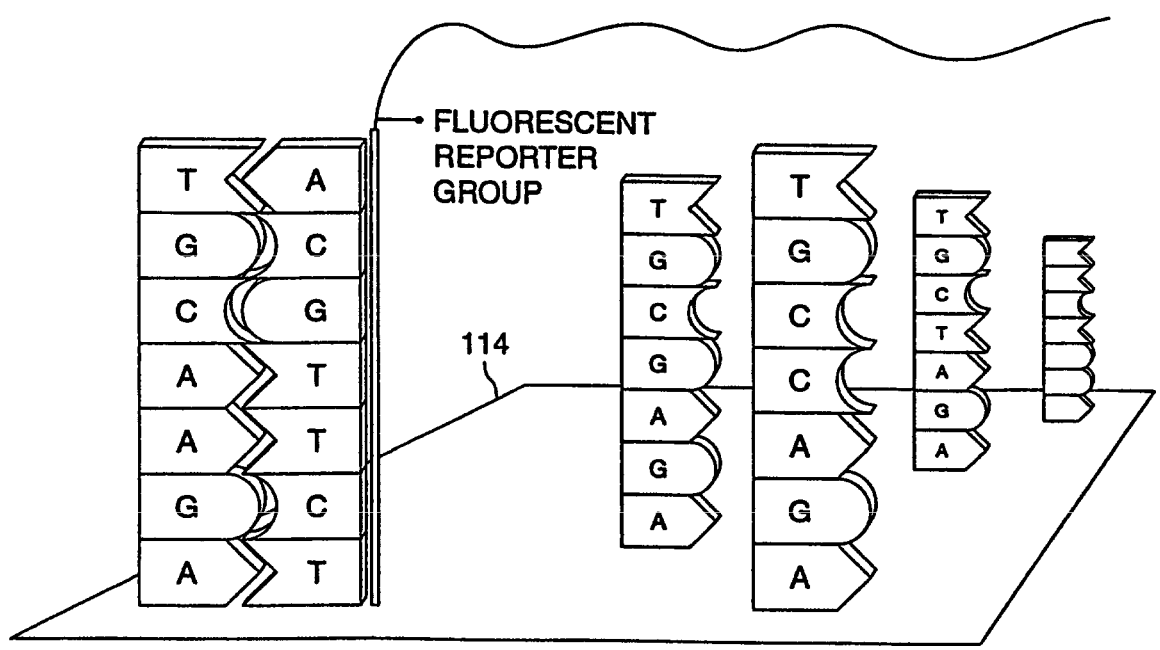
FIG. 5 illustrates conceptually the binding of probes on chips

FIG. 5 illustrates the binding of a particular target DNA to an array of DNA probes 114. As shown in this simple example, the following probes are formed in the array:

```
AGACCGT

AGAGCGT

AGATCGT
```

As shown, when the fluorescent-labeled (or otherwise marked) target 5'-TCTTGCA is exposed to the array, it is perfectly complementary only to the probe 3'-AGAACGT, and fluorescent will be primarily found on the surface of the chip where 3'-AGAACGT is located. The chip contains cells that include multiple copies of a particular probe. Thus, the image file will contain fluorescence intensities, one for each probe (or cell). By analyzing the fluorescence intensities associated with a specific probe, it becomes possible to extract sequence information from such arrays using the methods of the invention disclosed herein.

For ease of reference, one may call bases by assigning the bases the following codes:

| Code | Group | Meaning |
|---|---|---|
| A | A | Adenine |
| C | C | Cytosine |
| G | G | Guanine |
| T | T(U) | Thymine (Uracil) |
| M | A or C | aMino |
| R | A or G | puRine |
| W | A or T(U) | Weak interaction (2 H bonds) |
| Y | C or T(U) | pYrimidine |
| S | C or G | Strong interaction (3 H bonds) |
| K | G or T(U) | Keto |
| V | A, C or G | not T(U) |
| H | A, C or T(U) | not G |
| D | A, G or T(U) | not C |
| B | C, G or T(U) | not A |
| N | A, C, G, or T(U) | Insufficient intensity to call |
| X | A, C, G, or T(U) | Insufficient discrimination to call |

Most of the codes conform to the IUPAC standard. However, code N has been redefined and code X has been added.

Scanned Image Alignment

An overview of the process of scanned image alignment in general is included.

Figure 6:
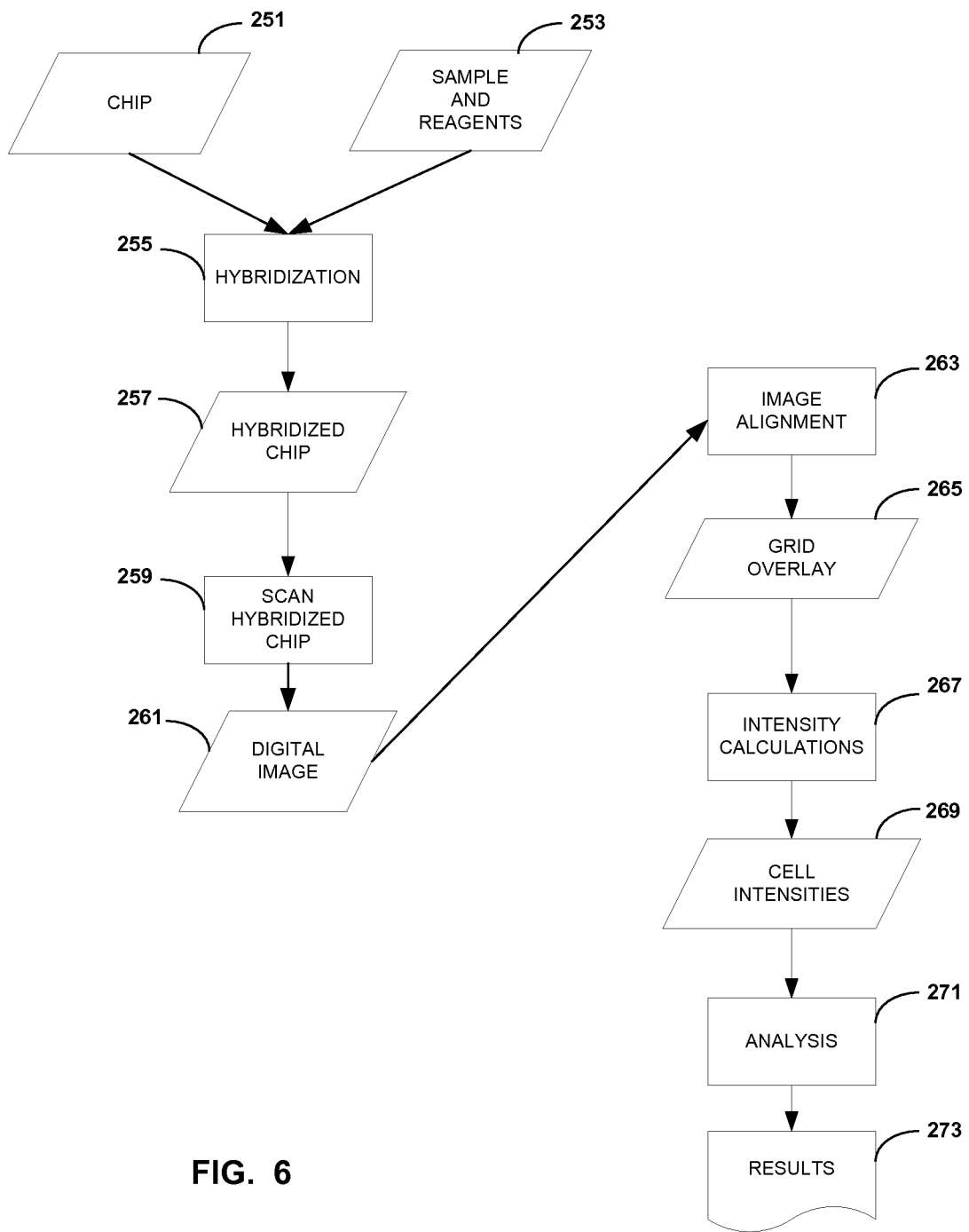
FIG. 6 illustrates a flowchart of how a chip is hybridized and analyzed to produce experimental results.

FIG. 6 illustrates a flowchart of a process of how a chip is hybridized and analyzed to produce experimental results. A chip 251 having attached nucleic acid sequences (or probes) is combined with a sample nucleic acid sequence (e.g., labeled fragments of the sample) and reagents in a hybridization step 255. The hybridization step produces a hybridized chip 257.

The hybridized chip is scanned at step 259. For example, the hybridized chip may be laser scanned to detect where fluorescent-labeled sample fragments have hybridized to the chip. Numerous techniques may be utilized to label the sample fragments and the scanning process will typically be performed according to the type of label utilized. The scanning step produces a digital image of the chip.

In preferred embodiments, the scanned image of the chip includes varying fluorescent intensities that correspond to the hybridization intensity or affinity of the sample to the probes in a cell. In order to achieve more accurate results, it is beneficial to identify the pixels that belong to each cell on the chip. At an image alignment step 263, the scanned image is aligned so that the pixels that correspond to each cell can be identified. Optionally, the image alignment step includes the alignment of a grid over the scanned image At a step 267, the analysis system analyzes the scanned image to calculate the relative hybridization intensities for each cell of interest on the chip. For example, the hybridization intensity for a cell, and therefore the relative hybridization affinity between the probe of the cell and the sample sequence, may be calculated as the mean of the pixel values within the cell. The pixel values may correspond to photon counts from the labeled hybridized sample fragments.

The cell intensities may be stored as a cell intensity file 269. In preferred embodiments, the cell intensity file includes a list of cell intensities for the cells. At an analysis step 271, the analysis system may analyze the cell intensity file and chip characteristics to generate results 273. The chip characteristics may be utilized to identify the probes that have been synthesized at each cell on the chip. By analyzing both the sequence of the probes and their hybridization intensities from the cell intensity file, the system is able to extract sequence information such as the location of mutations, deletions or insertions, or the sequence of the sample nucleic acid. Accordingly, the results may include sequence information, graphs of the hybridization intensities of probe(s), graphs of the differences between sequences, and the like. See, for example, U.S. Pat. No. 5,795,716, which is hereby incorporated by reference for all purposes.

Figure 7:
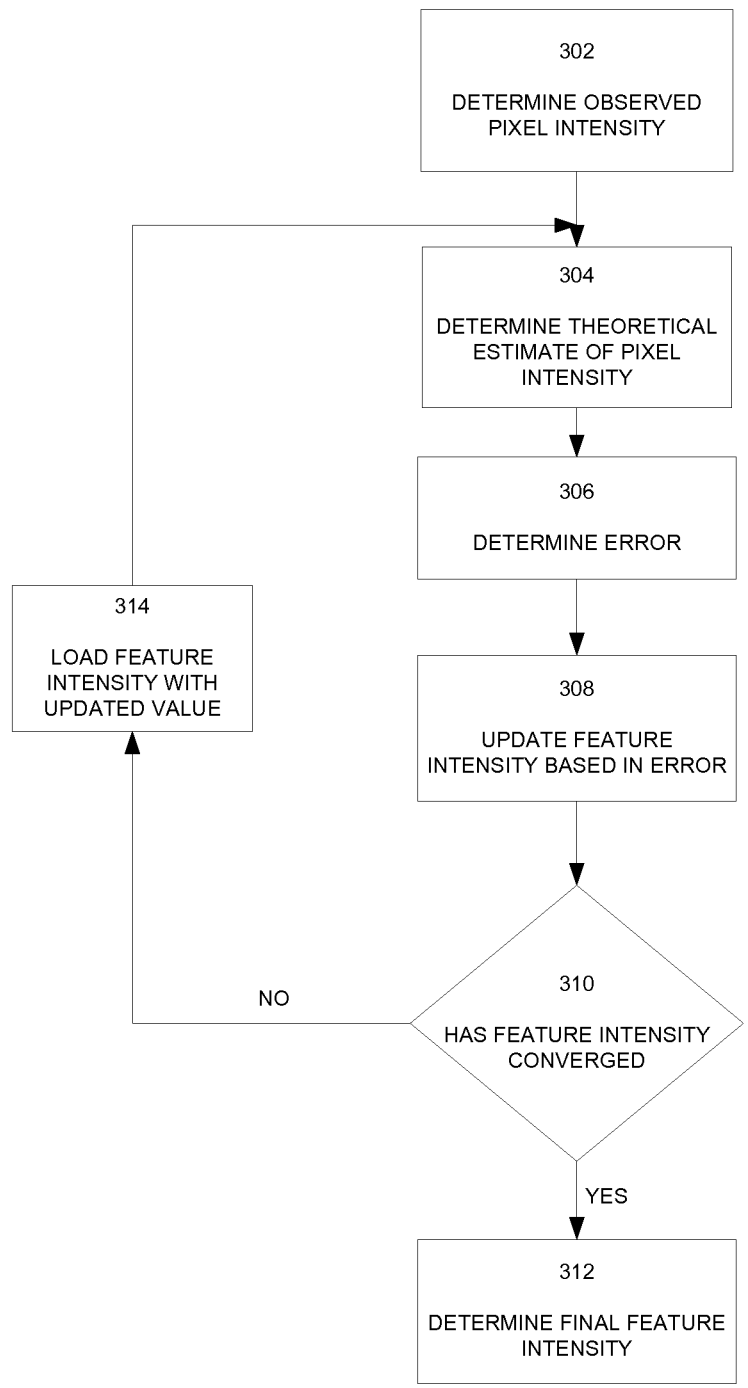
FIG. 7 shows a flowchart for a method of reconstructing feature intensities from pixel level data according to one illustrative embodiment of the invention.

FIG. 7 illustrates a flowchart of a method 300 of reconstructing feature intensities from pixel level data according to an illustrative embodiment of the invention. The method 300 determines hybridization intensities ("feature intensity") of each cell in a hybridized chip by iteratively updating the feature intensity based on a scanned image of the chip. The method 300 is a more detailed description of step 267 in FIG. 6. More particularly, method 300 begins with scanning an image and determining the observed intensity of each pixel on the scanned image of the chip (step 302). A scanned image typically comprises a plurality of pixels that represent a variation of intensities across the image. The pixels may be arranged as a grid comprising rows and columns and each pixel may have one value of intensity associated with it. The size of the pixel may vary depending on the technical specifications of the scanning instrument. Also, as noted earlier, a chip may comprise a plurality of cells arranged as a grid of rows and columns. Each cell may comprise a plurality of pixels arranged as a grid of rows and columns such that the variation of intensities across a set of pixels within a cell gives rise to a feature having a characteristic shape and intensity. Depending on the number of pixels representing a cell, the shape of the feature as well as the feature intensity may vary. The method 300 allows for the determination of a single feature intensity value for each cell utilizing the pixel intensities from the entire chip.

A theoretical estimate of the intensity of pixels on the scanned image of the chip may be made based on an initial estimate of a value for feature intensity and an initial estimate of the shape of the feature (step 304). The initial estimates for the value of the feature intensity and the initial estimates of the feature intensity may be empirically estimated. A theoretical estimate of the intensity may be made for all or substantially all pixels on the scanned image of the chip. A more detailed discussion of the calculation of the theoretical pixel intensity is provided with FIG. 8. An error may be calculated (step 306) for each pixel from the ratio of the observed pixel intensity measured in step 302 and the theoretical pixel intensity calculated in step 304. The error may also be adjusted such that outlier values are removed. FIG. 9 depicts particular steps related to the calculation of the error. Based on the calculated error for each pixel as well as the importance of each pixel in relation to a particular feature, the feature intensity for each feature may be corrected and a new value may be obtained (step 308). An update rule is described in more detail in relation to FIG. 10. The value of the feature intensity may then be checked to see if it has converged (step 310). In the event that the value of the feature intensity has not converged, the updated feature intensity value is entered for the calculation of the theoretical pixel intensity (step 314). Steps 304, 306, 308 and 310 are then repeated until convergence of feature intensity is obtained. The final value of the feature intensity is determined as the converged feature intensity value.

Figure 8:
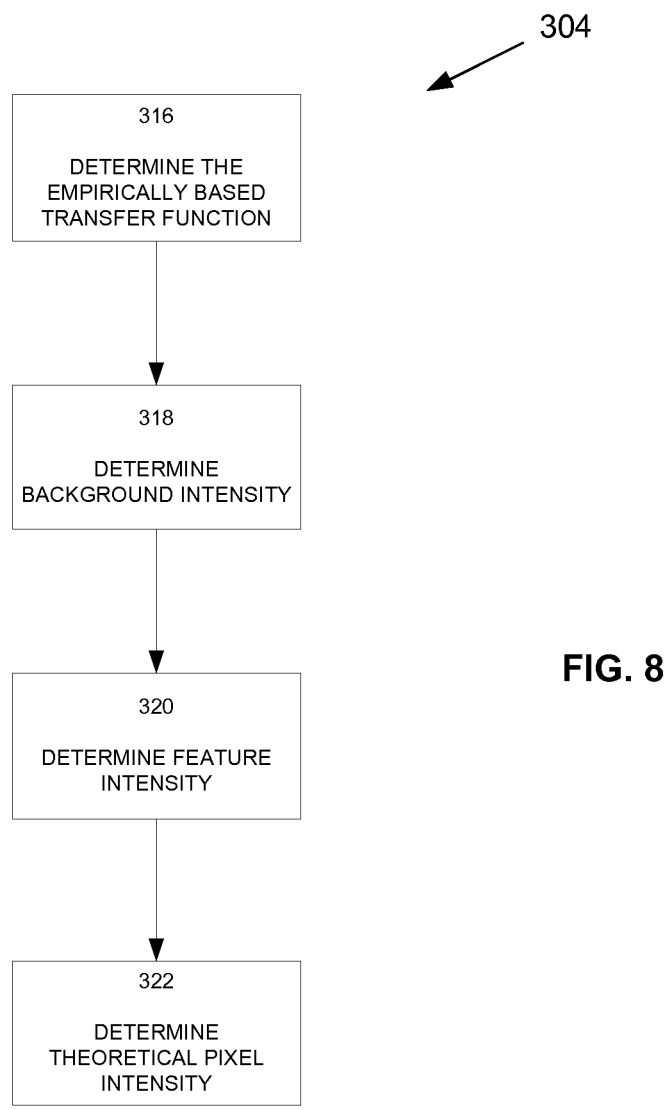
FIG. 8 shows a flowchart for a method of calculating the theoretical pixel intensity.
Figure 9:
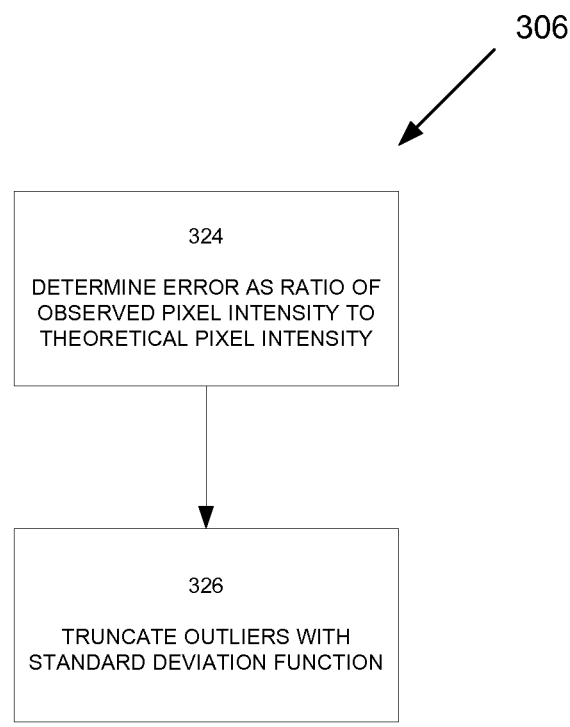
FIG. 9 shows a flowchart for a method of calculating an error based on the pixel level data and the theoretical pixel intensity.

FIG. 8 depicts the method 304 to calculate a theoretical estimate of the pixel intensities. The method 304 comprises the step of determining an empirically based transfer function that roughly relates to a shape of the feature (step 316). The transfer function relates the location of a pixel on the image with an intensity value. In one embodiment, the transfer function may comprise more than one value for each pixel on the image. In such an embodiment, a value for each pixel may be dependent on a feature on the chip. More particularly, a transfer function value for each pixel on the chip may be dependent on the feature intensities of a feature. In one embodiment, the transfer function may be a four-dimensional array comprising two dimensions relating to the pixel locations on a chip and two dimensions relating to address of the feature on which the value of each pixel is dependent. The transfer function may be empirically determined and may be typically initialized to any function. As an example, the transfer function, t, may be chosen to be as follows:

$$t(a,b)=1/(a^2+b^2+1) \quad [1]$$

Where a,b represent the distances in both a horizontal and vertical direction, respectively, from the center of a feature. The location of the center of the feature on the scanned image may be dependent on the location of the cell corresponding to the feature on the chip. In certain embodiments, the transfer function may be chosen such that it is greater than zero. In certain embodiments, the transfer function may be normalized such that the sum of all the values of the transfer function for the chip is about one.

The method 304 also includes the steps of calculating a value for background intensity (step 318) and an initial estimate for the feature intensity (step 320). In one embodiment, the background intensity may be chosen as the lowest observed pixel intensity larger than zero. The background intensity may be selected as other values without departing from the scope of the invention. In one embodiment, a single value of background intensity is chosen for the chip. As noted above, the feature intensity is a value corresponding to the hybridization intensity of a cell. In one embodiment, a single value of feature intensity is selected for a cell on the chip. In one embodiment, each cell may have different feature intensities.

A theoretical pixel intensity may then be estimated using the transfer function, background intensity and feature intensity values (step 322). In one embodiment, the theoretical pixel intensity may be calculated as the product of the transfer function and the feature intensity over the entire chip. The transfer function value of each pixel on the chip corresponding to a particular feature is multiplied with the feature intensity of the corresponding feature. In such an embodiment, the product of the transfer function and the feature intensity for each feature is summed over all the features. In one embodiment, a background intensity value may be added to each value of the theoretical pixel intensity. The operation of calculating the theoretical pixel intensity can be expressed mathematically as:

$$T(m,n)=\Sigma[t(m,n,x,y) \cdot I(x,y)]+B \quad [2]$$

Where, T(m,n) is the theoretical pixel intensity for each pixel (m,n), t(m,n,x,y) is the transfer function which is the proportion of intensity in pixel (m,n) due to feature in cell (x,y), I(x,y) is the feature intensity of a feature in cell (x,y) on the chip and B is the background intensity. The summation is performed over all cells (x,y).

FIG. 9 depicts a method 306 for calculating an error function. The method 306 comprises the steps of calculating a multiplicative error value as a ratio of the observed pixel intensity to the theoretical pixel intensity (step 324) and truncating the outlier values of error (step 326). In one embodiment, in step 324, the multiplicative error can be defined as shown in the mathematical expression below:

$$P(m,n) \cdot e(m,n)=T(m,n) \quad [3]$$

Where, P(m,n) is the observed pixel intensity for each pixel (m,n) on the chip, T(m,n) is the theoretical pixel intensity for each pixel (m,n) calculated according to equation 2 and e(m,n) is the multiplicative error. As shown in equation 3, the multiplicative error e(m,n) represents the multiplicative error of the observed pixel intensity on the scanned image of the chip. As an example, the intensity of hybridization of a DNA spot on a microarray is often used as a measure of gene expression, but the raw intensity is subject to a number of confounding error terms, such as DNA concentration in a spot and sequence hybridization efficiency. In such an example, these error terms may be modeled multiplicatively as e(m,n) in equation 3.

In one embodiment, the error e(m,n) may be randomly distributed over a cell and therefore the probability density function of the error may be of two-dimensional Gaussian form with the mean located near the center of a feature (cell) on the chip. Such an error model may be repeated for other features (cells) on the chip. A Gaussian form can imply that the error exponentially decreases from the center of the feature. In such embodiments, the error may be better modeled using a logarithmic function such that the error may be written as log [e(m,n)^2].

In another embodiment, the error may be modeled as the reciprocal of the error function e(m,n) shown in equation 3. In such an embodiment, error R(m,n) may be mathematically expressed as:

$$R(m,n)=P(m,n)/T(m,n) \quad [4]$$

Where R(m,n) is the error function for each pixel (m,n). The error R(m,n) may be randomly distributed in a two-dimensional Gaussian form.

The error R(m,n) may be adjusted to remove values of error that are far from an average error (step 326). A standard deviation function may be used to typically remove the outlier values. In one embodiment, the adjusted error may be calculated by comparing the error against a certain value. In such an embodiment, the value for comparison against the error may be chosen as, z, close to 1. In an exemplary embodiment, the value of z may be selected as 1.2. In such an embodiment, the error is restricted to lie within the range bound by z and 1/z. An exemplary function is shown below as:

$$S(m,n)=\max[\min\{R(m,n),z\},1/z] \quad [5]$$

Where S(m,n) is the adjusted error function for each pixel (m,n) on the chip. R(m,n) is error function as defined in equation 4 and z is value related to the standard deviation so that the adjusted error S(m,n) is restricted to a range defined by z and 1/z.

Figure 10:
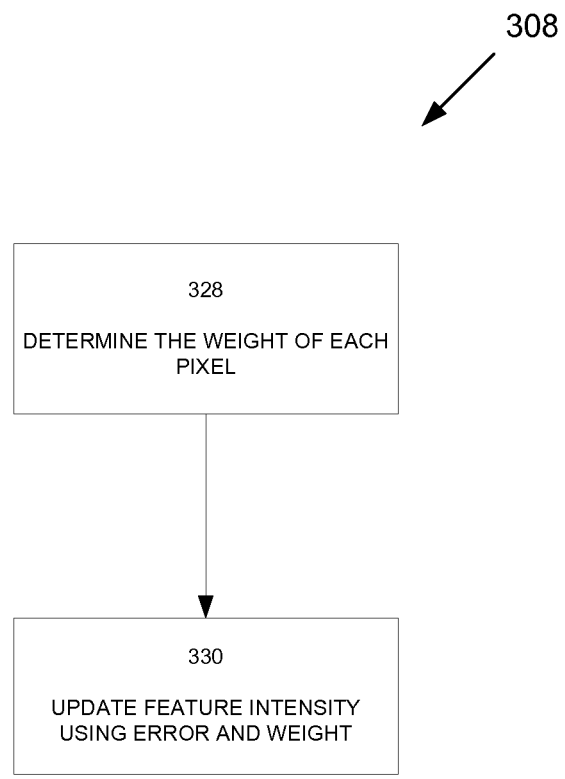
FIG. 10 shows a flowchart for a method of updating the feature intensities based on the error calculated in the method shown in FIG. 9

FIG. 10 depicts a method 308 for updating the feature intensity based on the adjusted error from FIG. 9. The method 308 comprises the steps of determining the importance of each pixel (step 328) and calculating a weight value for each, and then updating the feature intensity using the adjusted error and the calculated weight value (step 330). In one embodiment, in step 328, we can define a weight function to be the expected importance of a given pixel. In such an embodiment, the border pixels and mis-synthesized pixels may have lower weights assigned to them while pixels that are located near the center of each feature and those that play a relevant role in determining intensities may have higher weights assigned to them.

In step 330, the feature intensity may be adjusted by multiplying an update factor to a value of feature intensity calculated from a previous iteration. In one embodiment, the update factor may be calculated by multiplying an error function calculated from step 306 with the weight function calculated from step 328. As an example, the update factor may be mathematically written as:

$$U(x,y) = \Sigma[w(m,n) \cdot \log\{e(m,n)^2\}] \quad [6]$$

Where U(x,y) is the update factor for a cell (x,y) on the chip, w(m,n) is the weight assigned to each pixel (m,n), e(m,n) is the multiplicative error in each pixel (m,n) and the summation is performed over all pixels at a desired distance from the center of the cell. In certain embodiments, the summation is performed over all or substantially all pixels in a cell.

In the preferred embodiments, the update factor U(x,y) may be calculated using the adjusted error S(m,n) from equation 5. In such an embodiment, the update factor may be mathematically written as:

$$U(x,y) = \Sigma[w(m,n) \cdot S(m,n)]/\Sigma[w(m,n)] \quad [7]$$

Where U(x,y) is the update factor for a cell (x,y) on the chip, w(m,n) is the weight assigned to each pixel (m,n), S(m,n) is the adjusted multiplicative error in each pixel (m,n) and the summation is performed over all pixels at a desired distance from the center of the cell. Each cell (x,y) may have one or more pixels (m,n) included within. In certain embodiments, the summation is performed over all or substantially all pixels in a cell.

Also, in step 330, the update factor is used to update the value of the feature intensity. In one embodiment, the update factor from equation 7 is multiplied to the feature intensity to determine a new value for feature intensity.

$$I(x,y)(k) = I(x,y)(k-1) \cdot U(x,y) \quad [8]$$

Where I(x,y)(k) is unobserved feature intensity of feature (x,y) at iteration index k. The iteration index k is a counter that keeps track of variables such as the feature intensity at the end of each iteration. Therefore, I(x,y)(k-1) is unobserved feature intensity of feature (x,y) at iteration index k-1. The feature intensity I(x,y)(k-1) is the feature intensity at the end of the previous iteration. U(x,y) is the update factor including a pixel weighting term and a pixel error term.

In alternate embodiments, the update factor may be used to update the value of the transfer function. In such an embodiment, the update factor from equation 7 is multiplied to the transfer function from equation 1. The ability of the method 300 to update of the transfer function permits minimum assumption involving the shape of the feature.

In another embodiment the update factor may be used to update the value of the background intensity. In such an embodiment, the update factor from equation 7 is multiplied to the background intensity, B, shown in equation 2.

In the above discussion, it was assumed that the center of the feature and the center of the cell corresponding to the feature are nearly overlapping. However, in certain situations, the center of a feature may be different from the center of the cell. The logarithmic error calculation discussed in the description of FIG. 9 and shown in equation 6 may be used to update the location of the feature center points. In such cases the update factor similar to one shown in equation 6 may be used to update the centers of the feature (x,y). In one embodiment, an iterative update step may be included in method 300 that updates the center of the feature. The update factor may also be simplified in such cases as:

$$U(x,y) = \Sigma[\log\{S(m,n)^2\}] \quad [9]$$

Where U(x,y) is the update factor for a cell (x,y) and S(m,n) is the adjusted error for each pixel (m,n) and the summation is performed over all pixels at a desired distance from the center of the cell. Each cell (x,y) may have one or more pixels (m,n) included within. In certain embodiments, the summation is performed over all or substantially all pixels in a cell.

In many embodiments of the invention, if the method 300 begins with positive values for feature intensity, transfer function and background intensity, then the final values for feature intensity, transfer function and background intensity remain positive. In such embodiments, the positive nature is maintained due, at least in part, to the use of a multiplicative error model. In certain embodiments, if the transfer function and background intensity were fixed during the updating process and only the feature intensity was chosen to be updated, then the feature intensity typically converges to a unique value. In such embodiments, the convergence is typically obtained within a few iterations.

Figure 11A:
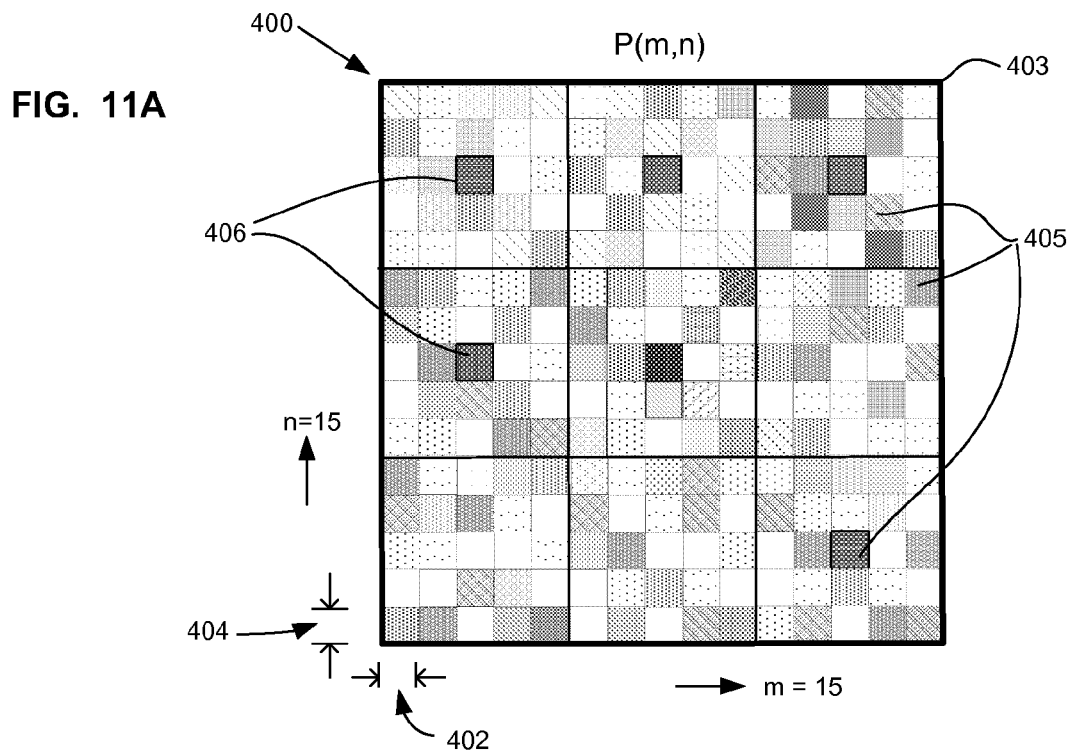
FIGS. 11A and 11B show examples of pixel intensity and feature intensity charts.
Figure 11B:
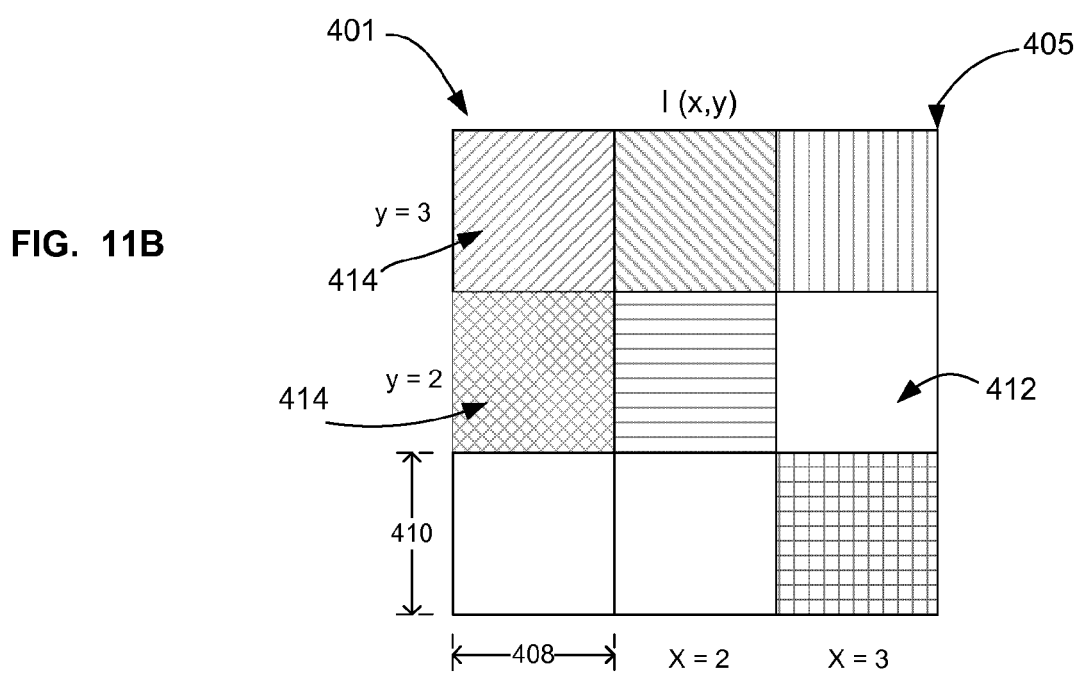

FIGS. 11A and 11B are visualizations of examples of the pixel intensity and the feature intensity, respectively according to the method of the invention. FIG. 11A shows the observed pixel intensity chart 400 for a scanned image file 403 of microarray chip. The observed pixel intensity chart 400 is divided into a grid of pixels 405 each having length dimension 402 and width dimension 404. The observed pixel intensity chart comprises about 225 pixels with fifteen pixels along the horizontal length dimension and about 15 pixels along the vertical width dimension. Each pixel 405 is shaded according the intensity of brightness measurement obtained from a fluorescence measurement. Darker shaded pixels are shown to have a higher intensity than lighter shaded pixels. Each of the darkest shaded pixels 406 corresponds to the center of a hybridization intensity feature. In the illustrated embodiment, six centers of feature intensity are depicted asymmetrically spaced out. In this example, as we move away from the high intensity feature center, the intensity value of the pixels begins to fall. Pixels with the lightest shading may depict areas where hybridization has not occurred. The pixel intensity of such light shaded pixels may be termed as background intensity.

In other embodiments, the scanned image file 403 may comprise a different number of pixels having different dimensions to the illustrated embodiment. In other embodiments, the there may be more or less feature centers and each pixel may have a different intensity value without departing from the scope of the invention.

FIG. 11B shows the unobserved feature intensity chart 401 for a scanned image file 403. The unobserved feature intensity chart 401 is divided into a grid of cells 414 each having length dimension 408 and width dimension 410. The unobserved feature intensity chart 401 is shown to comprise of three cells in the horizontal length dimension and three cells in the vertical width direction. Each cell 414 is shaded according to feature intensity value. The feature intensity value corresponds to the single value associated with the intensity of a particular feature. Similar to the number of feature centers 406 shown in FIG. 11A, there are six cells that are shaded. Cells 412 are not shaded since those cells represent blank cells where a nucleic acid probe may have been absent.

Method 300 of FIG. 7 depicts a process to reconstruct an unobserved feature intensity chart 401 of FIG. 11B from an observed pixel intensity chart 400 of FIG. 11A. In one embodiment, the pixels nearest to the feature center 406 may be averaged to obtain a suitable intensity value for cell. In such an embodiment, each cell may be associated with 25 pixels such that there are five pixels in the horizontal direction and five pixels in the vertical direction. For each cell, the averaging may then be performed over the 25 pixels such that nine values related to the feature intensities may emerge. However, in such embodiments, each pixel is weighted equally and the observed pixel intensity of each pixel is assumed to be dependent only on one feature, namely the nearest feature. Furthermore, if cell sizes are made smaller such that fewer pixels are included in each cell then, the averaging is performed over fewer pixels. Method 300 overcomes these limitations by utilizing a transfer function.

Figure 12A:
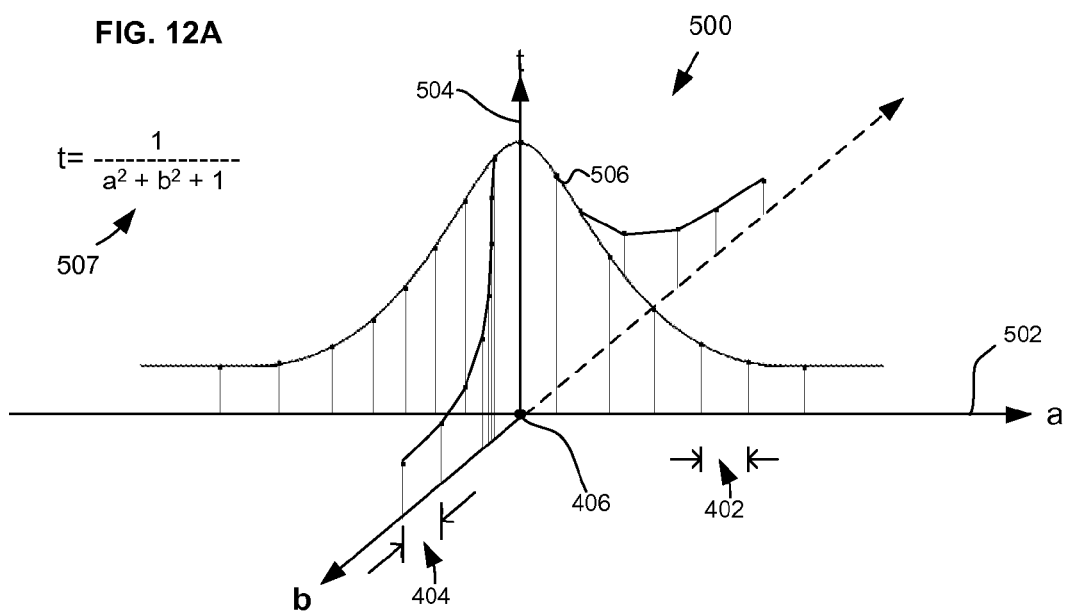
FIGS. 12A and 12B show an example of a transfer function used to calculate the theoretical pixel intensity.
Figure 12B:
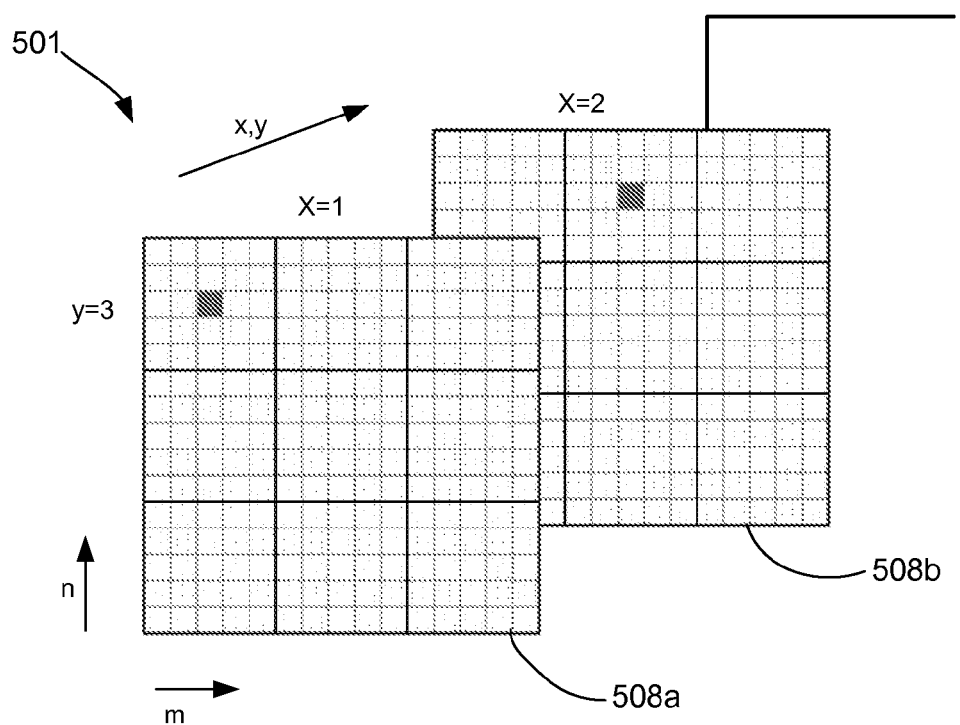

FIGS. 12A and 12B depict visualizations of the transfer function according to an illustrative embodiment of the invention. FIG. 12A is a graph showing a transfer function for a feature according to equation 1. The origin of the graph is typically made to coincide with the center of a feature 406. The horizontal axis 502 corresponds to the horizontal axis of the image file. The vertical axis 504 corresponds to the vertical axis of the image file. The distance between transfer function values on the horizontal axis may be chosen such that it is made approximately equal to the pixel length 402 and the distance between transfer function values on the vertical axis may be chosen such that it is made approximately equal to the pixel width 404. The plot 506 shows that as we move away from the center of the feature, the transfer function value decreases according to equation the shown (507).

FIG. 12B depicts transfer function intensity charts 501 comprising transfer function image files 508*a* and 508*b* (generally "image file 508"). Transfer function image file 508*a* shows intensity values for each pixel that is calculated due to a particular feature. Referring back to FIGS. 11A and 11B, the image file 508 also comprises pixels that are distributed in a grid of dimensions fifteen along the horizontal axis and fifteen along the vertical axis. Each pixel in image file 508*a* has an intensity that is a proportion of the pixel intensity due to feature approximately located on the top left corner. In terms of cells 412 of FIG. 11B, the intensity of pixels in the image file 508*a* is due to the feature within the cell given by x position 1 and y position 3. Each pixel in image file 508*b* has an intensity that is a proportion of the pixel intensity due to the feature within the cell given by x position 2 and y position 3. In one embodiment, a plurality of image files 508 may be included within the transfer function intensity chart 501 such that each image file 508 corresponds to a particular feature on the chip. In the above embodiment, one may have nine image files that correspond to nine cells.

Referring back to method 300 of FIG. 7, in step 304, background intensity may be estimated as the lowest intensity observed in the pixel intensity chart 400. Each of the image files 508 of the transfer function intensity chart 501 may be multiplied by a feature intensity chart 401 similar to one shown in FIG. 11B to form product image files. Following multiplication, the product image files may be summed together. Initially, the feature intensity chart 401 may be chosen as such that the feature intensity of each cell is approximately equal to the average of the pixel intensities of the pixels within the cell. The background intensity may be added to the summed product image file to give a theoretical pixel intensity chart. The error may be determined by dividing the pixel intensity chart 400 by the theoretical pixel intensity chart.

It is to be understood that the above description is intended to be illustrative and not restrictive. Many variations of the invention will be apparent to those of skill in the art upon reviewing the above description. The scope of the invention should be determined with reference to the appended claims, along with the full scope of equivalents to which such claims are entitled. All cited references, including patent and non-patent literature, are incorporated herewith by reference in their entireties for all purposes.

We claim:

1. A computer-implemented method of determining feature intensities from image data from a probe array, the method comprising:
   a. obtaining image data for a plurality of features of the probe array, wherein the image data comprises a set of pixels, wherein the set of pixels comprises groups of pixels associated with each feature, wherein the groups are aligned with each feature, wherein the groups of pixels indicate a center pixel for each feature;
   b. determining observed pixel intensities for one or more pixels in the set of pixels;
   c. determining initial feature intensities for the plurality of features, wherein the initial feature intensities are based upon the observed pixel intensities;
   d. determining a theoretical pixel intensity for one or more pixels in the set of pixels from feature intensities of one or more of the plurality of features;
   e. determining an error for each pixel in the set of pixels, wherein the error is based upon the observed pixel intensity and the theoretical pixel intensity; and
   f. determining a corrected feature intensity for the plurality of features, wherein the corrected feature intensity is based upon a previously determined feature intensity and the error, and
   g. repeating steps d-f comparing the corrected feature intensities against previously determined feature intensities until the corrected feature intensities converge; and
   h. after convergence, outputting the adjusted feature intensities.

2. The method of claim 1,
   wherein the theoretical pixel intensities are based, at least in part, upon a plurality of feature intensities;
   wherein determining the theoretical pixel intensity comprises determining an empirically based transfer function, and
   wherein determining the theoretical pixel intensity comprises multiplying the empirically based transfer function with a plurality of feature intensities.

3. The method of claim 2, wherein the empirically based transfer function relates to a shape formed by of pixels associated with a feature.

4. The method of claim 2, wherein the empirically based transfer function relates for each pixel, the location of the pixel within the image data with feature intensities.

5. The method of claim 2, wherein the empirically based transfer function comprises an array, and wherein the array comprises dimensions relating to pixel locations and dimensions relating to an address of a plurality of features.

6. The method of claim 3, wherein the empirically based transfer function is based upon representation of a pixel location relative to a center location of a plurality of features.

7. The method of claim 2, wherein determining the theoretical pixel intensity additionally comprises determining a background intensity.

8. The method of claim 7, wherein the background intensity is added to an initial theoretical pixel intensity to determine the theoretical pixel intensity.

9. The method of claim 1, wherein determining the error comprises calculating a multiplicative error value based upon the observed pixel intensity and the theoretical pixel intensity.

10. The method of claim 9, wherein calculating the multiplicative error value comprises determining an error function based upon the observed pixel intensity and the theoretical pixel intensity.

11. The method of claim 10, wherein the error function is the quotient of dividing the observed pixel intensity by the theoretical pixel intensity.

12. The method of claim 10, wherein the error function is adjusted to remove outlying error values.

13. The method of claim 12, wherein the outlying error values are removed with use of a standard deviation function.

14. The method of claim 12, wherein determining the adjusted feature intensity comprises multiplying the initial feature intensity by an update factor, and wherein the update factor is based upon the error function after adjustment to remove outlying error values.

15. The method of claim 10, wherein the error function is adjusted through comparison to a preselected value.

16. The method of claim 15, wherein the error function is restricted within a preselected range, wherein the preselected range is defined by the preselected value and 1/preselected value.

17. The method of claim 1, wherein determining the adjusted feature intensity comprises multiplying the initial feature intensity by an update factor, and wherein the update factor is based upon the error.

18. The method of claim 17, wherein the update factor is additionally based upon a weight function, wherein each feature comprises a center location, and wherein the weight function assigns a weight to a pixel based upon the pixel's distance from the center location such that pixels are assigned a higher weight as their distance from the center location decreases.

19. The method of claim 1, further comprising:
repeating the determining a theoretical pixel intensity, determining an error for each pixel in the set of pixels, and determining feature intensity steps until the adjusted feature intensity has converged, wherein the repeated third through fifth determining steps utilize the corrected feature intensity in place of the initial feature intensity.

20. The method of claim 1, wherein determining an observed pixel intensity step, the determining an initial feature intensity step, the determining a theoretical pixel intensity step, the determining an error for each pixel in the set of pixels step, and the determining an adjusted feature intensity step are performed by a computer processor located on a computer.

* * * * *